(12) United States Patent
Dumont et al.

(10) Patent No.: US 11,883,631 B2
(45) Date of Patent: *Jan. 30, 2024

(54) METHODS AND SYSTEMS FOR CLOSED-LOOP CONTROL OF DRUG ADMINISTRATION

(71) Applicant: The University of British Columbia, Vancouver (CA)

(72) Inventors: Guy Dumont, Vancouver (CA); Mark Ansermino, Vancouver (CA); Sara Khosravi, Burnaby (CA); Nicholas West, Littlehampton (GB)

(73) Assignee: The University of British Columbia, Vancouver (CA)

( * ) Notice: Subject to any disclaimer, the term of this patent is extended or adjusted under 35 U.S.C. 154(b) by 59 days.

This patent is subject to a terminal disclaimer.

(21) Appl. No.: 17/590,017

(22) Filed: Feb. 1, 2022

(65) Prior Publication Data
US 2022/0211943 A1 Jul. 7, 2022

Related U.S. Application Data

(63) Continuation of application No. 15/979,661, filed as application No. PCT/CA2016/051375 on Nov. 23, 2016, now Pat. No. 11,266,780.

(Continued)

(51) Int. Cl.
*A61M 5/142* (2006.01)
*A61M 5/172* (2006.01)
(Continued)

(52) U.S. Cl.
CPC .............. *A61M 5/1723* (2013.01); *A61B 5/00* (2013.01); *A61B 5/369* (2021.01); *A61B 5/4821* (2013.01);
(Continued)

(58) Field of Classification Search
CPC ...... A61M 5/1723; A61M 2005/14296; A61M 2202/048; A61B 5/4821; A61B 5/4839;
(Continued)

(56) References Cited

U.S. PATENT DOCUMENTS 9,849,241 B2 * 12/2017 Becker ................... G16H 20/17

OTHER PUBLICATIONS

"Sawaguchi, A Model-Predictive Hypnosis Control System Under Total Intravenous Anesthesia, Mar. 2008. IEEE Transactions on Biomedical Engineering, vol. 55 No. 3, (pp. 874-887)" (Year: 2008).*

* cited by examiner

*Primary Examiner* — Nathan R Price
*Assistant Examiner* — Tania Ismail
(74) *Attorney, Agent, or Firm* — Brian Kolkowski

(57) ABSTRACT

A control system for administration of a drug comprises a drug administration actuator for administering the drug to a patient at a controllable dosage; a monitor for measuring an effect of the drug on the patient; and a controller configured to determine a control signal to the drug administration actuator; wherein the controller is configured to implement a closed loop model-predictive control scheme comprising, for each of a series of time steps, minimizing a cost function subject to one or more constraints to determine the control signal, the cost function based at least in part on a reference level and the monitor measurement; wherein the control signal is used as an input to an auxiliary model to estimate at least one concentration level of the drug in the patient; and wherein the constraints comprise at least one constraint on the estimate of the concentration level of the drug.

20 Claims, 15 Drawing Sheets

Related U.S. Application Data

(60) Provisional application No. 62/258,656, filed on Nov. 23, 2015.

(51) Int. Cl.
  *A61B 5/00*    (2006.01)
  *A61B 5/369*   (2021.01)
  *G16H 20/13*   (2018.01)
  *A61M 5/14*    (2006.01)

(52) U.S. Cl.
  CPC ............ *A61B 5/4839* (2013.01); *A61B 5/725* (2013.01); *A61M 5/172* (2013.01); *G16H 20/13* (2018.01); *A61M 5/14* (2013.01); *A61M 2005/14296* (2013.01); *A61M 2202/048* (2013.01); *A61M 2205/3303* (2013.01); *A61M 2205/50* (2013.01); *A61M 2230/06* (2013.01); *A61M 2230/10* (2013.01); *A61M 2230/30* (2013.01); *A61M 2230/42* (2013.01); *A61M 2230/43* (2013.01)

(58) Field of Classification Search
  CPC .. A61B 5/369; A61B 5/00; A61B 5/14; G16H 20/13
  See application file for complete search history.

METHODS AND SYSTEMS FOR CLOSED-LOOP CONTROL OF DRUG ADMINISTRATION

REFERENCE TO RELATED APPLICATIONS

This application is a continuation of U.S. patent application Ser. No. 15/979,661, which was filed on May 15, 2018 and which is a National Stage application claiming priority to International application serial number PCT/CA2016/03175, filed on Nov. 23, 2016, which claims priority from U.S. Application No. 62/258,656 filed on 23 Nov. 2015 and entitled PHYSIOLOGICALLY SAFE CLOSED-LOOP CONTROL OF ANESTHESIA VIA MPC. For purposes of the United States, this application claims the benefit under 35 U.S.C. § 119 of U.S. Application No. 62/258,656 filed on 23 Nov. 2015 and entitled PHYSIOLOGICALLY SAFE CLOSED-LOOP CONTROL OF ANESTHESIA VIA MPC which is hereby incorporated herein by reference for all purposes.

TECHNICAL FIELD

This technology relates to systems and methods to control the infusion of agents administered into the body. Particular embodiments relate to closed-loop control of anesthesia infusion.

BACKGROUND

Total intravenous anesthesia typically involves continuous infusion of at least two carefully titrated drugs: one to suppress consciousness (a hypnotic, such as propofol) and one to suppress response to painful stimuli (an analgesic, such as remifentanil). Typically these drugs are infused by syringe pumps which are manually programmed to deliver a fixed drug infusion rate based on patient body weight, among other factors. However, individual patient response to these drugs varies highly across patients, situations (e.g., extreme bleeding), and changes with prolonged infusion. Anesthesiologists typically manually adjust dosing to account for this variability, based on their observations of feedback from physiological measures. Effective and safe manual anesthesia requires considerable clinical experience and thorough understanding of the transport, metabolism and temporal effects of the drugs.

Automatic control of anesthesia can assist the anesthesiologist by administering the appropriate drug dosage to keep the patient at an adequate level of anesthesia, reducing the effect of patient variability and providing fast rejection of surgical stimuli (as described, for example, in Gentilini, A., M. Rossoni-Gerosa, et al. (2001), "*Modeling and closed-loop control of hypnosis by means of bispectral index (BIS) with isoflurane*", Biomedical Engineering, IEEE Transactions on 48(8): 874-889; Struys, M. D. P. D. Michel M. R. F., M. S. T. De Smet, et al. (2001), "*Comparison of Closed-loop Controlled Administration of Propofol Using Bispectral Index as the Controlled Variable versus 'Standard Practice' Controlled Administration*", The Journal of the American Society of Anesthesiologists 95(1): 6-17; and Dumont, G. A., Martinez, A., Ansermino, J. M. (2008), "*Robust control of depth of anesthesia*", Int. J. Adapt. control Signal Process 23: 435-454 ("Dumont 2008"). Closed-loop control of anesthesia uses a physiological measure of the effect of drug infusion as feedback to continuously adjust drug infusion rates, resulting in individualized drug infusion constantly optimized to clinical circumstance. Experimental systems have shown that closed-loop control of anesthesia has the potential to improve patient safety by reducing variability in the desired drug effect, overall drug quantities required, and instances of overdose. Furthermore, such systems may reduce variation in clinical practice, offering the opportunity to improve clinical outcomes (see Kheterpal, M. D. M. B. A. S. (2012), "*Random Clinical Decisions Identifying Variation in Perioperative Care*", The Journal of the American Society of Anesthesiologists 116 (1): 3-5; and Mackey, M. D. David C. (2012), "*Can We Finally Conquer the Problem of Medical Quality? The Systems-based Opportunities of Data Registries and Medical Teamwork*", The Journal of the American Society of Anesthesiologists 117(2): 225-226. A significant difficulty in the design of controllers for closed-loop control of anesthesia is the significant intra- and inter-patient variability that is observed in response to a standard dose of drug. This has led to concern about the safety of closed-loop control systems in anesthesia (as discussed for example in Bibian, S., C. R. Ries, et al. (2005), "*Introduction to Automated Drug Delivery in Clinical Anesthesia*", European Journal of Control 11(6): 535-557).

It is desirable that closed-loop control systems for anesthesia incorporate safety constraints on estimated drug concentrations and magnitude of infusion rates. The constraints can be due the physical hard constraints on the system and/or may be defined based on the therapeutic window of the anesthesia drug (see K. van Heusden, N. W., A. Umedaly, J. M. Ansermino, R. N. Merchant, and G. A. Dumont (2014), "Safety, constraints and anti-windup in closed-loop anesthesia", 19th IFAC World Congress: 6569-6574 ("van Heusden et al. 2014")). During surgical procedures, a combination of hypnotic anesthetic drugs and opioid (analgesic) drugs is typically administered by an anesthesiologist to induce hypnosis and to attenuate the natural response to injury. Consequently, there is a desire to control anesthesia by controlling both hypnosis and analgesia with safety constraints incorporated in the controller design.

Model Predictive Controller (MPC) control strategy offers solutions for the regulation of constrained linear or nonlinear systems, as discussed for example in Maciejowski, J. M. (2002), "Predictive control with restraints", Prentice Hall ("Maciejowski 2002"). MPC control strategy has the inherent ability to handle multivariable control problems and to allow constraints to be imposed on both the controlled and manipulated variables. MPC has been successfully implemented in many applications in the chemical industry (see, for example, Qin, S. J., Badgwell, T. A (1997), "*An overview of industrial models predictive control technology*", Automatica 93(316): 232-256) and use of MPC has been proposed for the control of blood glucose (see Cobelli, C., C. D. Man, et al. (2009), "*Diabetes: Models, Signals, and Control*" IEEE reviews in biomedical engineering 2: 54-96) and anesthesia drugs (see Ionescu, C. M., R. De Keyser, et al. (2008), "*Robust Predictive Control Strategy Applied for Propofol Dosing Using BIS as a Controlled Variable During Anesthesia*," Biomedical Engineering, IEEE Transactions on 55(9): 2161-2170 ("Ionescu, De Keyser et al. 2008"); Sawaguchi, Y., E. Furutani, et al. (2008), "*A Model-Predictive Hypnosis Control System Under Total Intravenous Anesthesia*", Biomedical Engineering, IEEE Transactions on 55(3): 874-887 ("Sawaguchi, Furutani et al. 2008"); and Niño, J., R. De Keyser, et al. (2009), "*EPSAC-controlled anesthesia with online gain adaptation*," International Journal of Adaptive Control and Signal Processing 23(5): 455-471 ("Nino, De Keyser, et al. 2009")). In the field of anesthesia, an advantage of MPC is that it provides the ability to control both hypnosis and analgesia, with constraints on drug infusion rates and predicted drug concentrations. Closed-loop control of hypnosis using MPC in adults has been evaluated in simulation (in Ionescu, De Keyser, et al., 2008, and Nino, Keyser, et al. 2009) as well as in a clinical study (in Sawaguchi, Furutani, et al. 2008). A control system using an individualized MPC controller augmented by a "risk control" supervisory system was evaluated in 79 clinical cases in Sawaguchi, Furutani et al., 2008. Induction of anesthesia was manually controlled and the measured response was used to identify model parameters for the individualized MPC controller. The proposed controller was evaluated in simulation prior to the study, where plant-model mismatches were introduced. However, formulation of robust stability and performance guarantees for this adaptive approach is technically challenging. An extended prediction self-adaptive control algorithm (EPSAC) was compared to an adaptive controller in simulation (see Ionescu, De Keyser et al. 2008). The dynamics of the models do not take the inter-patient variability observed in pharmacokinetic-pharmacodynamic (PKPD) studies into account, and the uncertainty description used in this study possibly underestimates the variability observed in practice.

Safety bounds on estimated drug concentrations and magnitude of infusion rates have been included in a number of experimental systems for closed-loop control of anesthesia (see, for example, Sawaguchi, Furutani et al. 2008; van Heusden et al. 2014). Van Heusden et al. investigated a number of scenarios encountered in anesthesia practice where there is an obvious need for safety. The constraints were defined based on the therapeutic window of propofol and were implemented in a PID closed-loop system with anti-windup (see van Heusden et al. 2014). A control system using an individualized model predictive control (MPC) controller plus a "risk control" supervisory system was employed by Sawaguchi, Furutani et al. during a study of closed-loop control of hypnosis. Sawaguchi, Furutani et al. implemented the supervisory system to imitate counter measures taken by anesthesiologists for undesirable states such as intraoperative arousal, hypotension (low blood pressure), and bradycardia (heart rate under 60 beats per minute) (see Sawaguchi, Furutani et al. 2008).

Significant challenges in closed-loop control of the delivery of liquid agents or medications that are administered into the patient's body (e.g. intravenously, by inhalation, or otherwise) arise from the inter-patient uncertainty in the patient's response to the agent. There is a general desire for technology including an MPC based on robust control principles that addresses and/or ameliorates at least some of the aforementioned problems and/or improves the physiological safety of patients and efficacy of the delivery of anesthesia and other agents.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the technology relates to robust and constrained MPC controllers for closed-loop control of infusion of agents in adults and children. The MPC is based on a nominal model and integrates one or more auxiliary models (such as a population-based PKPD model of a physiological characteristic) that is used to handle constraints on the drug concentration level within a patient or the one or more physiological characteristics on which the model is based. Minimization of an MPC performance index can be performed subject to constraints on the drug infusion rate (which may be a hard physical constraint based on the maximum infusion rate of the syringe pump, or a patient safety constraint that is based on the therapeutic window of the particular drug being delivered), the estimated drug plasma concentration and/or the estimated effect site concentration (which may be derived from the auxiliary model), and/or measurable physiological pressures (such as systolic blood pressure), and/or combined with constraints provided by the one or more auxiliary models to determine the optimized drug infusion rate. The technology has particular application for the control of infusion of anesthetic agents, including hypnotics and analgesics, which are delivered to a patient through intravenous injection, inhalation or other means. Other embodiments can be applied to control infusion of other types of agents, including for example, neuromuscular-blocking agents (which can be used in conjunction with anesthesia to prevent involuntary movement), hemodynamic medications, antihypertensive agents, analgesic adjuvants, neuroprotective drugs, anti-inflammatory agents and/or the like. In some embodiments, the MPC controller is a multivariable MPC controller that controls the infusion of more than one agent administered into the body.

Another aspect of the technology provides for the use of auxiliary models in a closed-loop control system to model the effect of an infused drug on a physiological characteristic within a patient, and project certain constraints back into the input space of the robust MPC controller when performing the MPC optimization. In some embodiments, the physiological characteristic may comprise one or more of: depth of hypnosis, blood pressure, cardiac output, heart rate variability, end tidal $CO_2$, respiratory rate, minute ventilation, end-tidal anesthetic agent monitoring and/or the like. The auxiliary model may be linear or nonlinear, and may have the form of a transfer function, state-space model or any form of data-driven model. The auxiliary model may comprise a PKPD model, a population-based PKPD model, a patient-specific PKPD model (e.g. based on the patient's history), a multi-compartment PKPD model, a Kalman filter, and/or the like.

A further aspect of the technology relates to the use of an actual measurement of a measurable physiological characteristic of the patient. The auxiliary model is modified such that a Kalman filter, a state observer or similar method is used to estimate the next prediction of the physiological characteristic to provide the constraint to the MPC to find the optimized drug infusion rate.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Figure 1:
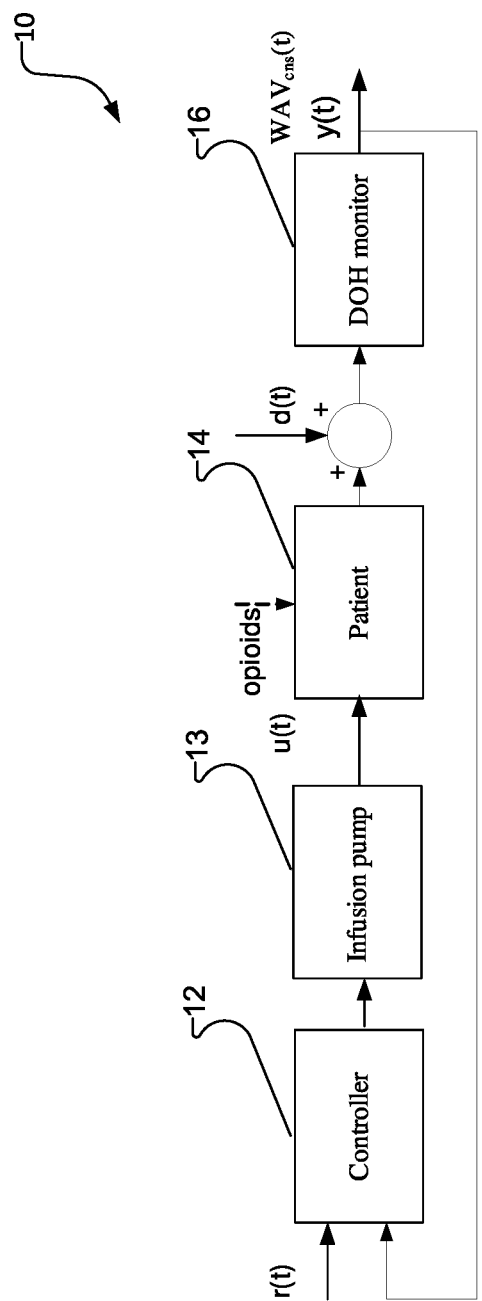
FIG. 1 is a block diagram of a closed loop system for controlling the delivery of a drug.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Model Predictive Control (MPC) is a type of control technique used for process control applications. An advantage of MPC is that it allows control under constraints. In addition to handling constraints on the control signal, MPC can be used in a state-space form to handle constraints on state variables that do or do not have a physical meaning. In particular embodiments, closed-loop control of the administration of anesthesia using MPC is based on a pharmacokinetic-pharmacodynamic (PKPD) model in which the controller states represent various concentrations (e.g. the plasma and/or effect site concentrations of the drug), and the closed-loop control is subject to safety-driven constraints on these concentrations.

Significant inter-patient uncertainty (resulting from the variability in patients' response to the delivered drug(s)) presents challenges in designing a closed-loop controller for delivery of anesthesia drug infusion. To address these challenges, robust control principles may be applied to the design of an MPC for control of anesthesia infusion. To robustly tune a MPC controller based on an existing bank of representative patient models, one may first derive a nominal model and characterize the uncertainty of this model due to inter-patient variability. Then a controller may be designed to meet performance requirements for the defined uncertainty around the nominal model. A challenge associated with this methodology is that the nominal model loses the PKPD structure and the controller states no longer represent concentrations. The inventors of the present application have addressed this problem by integrating, in an MPC controller, an auxiliary model (such as a population-based PKPD model) to compute concentrations and project concentration constraints back into the input space of the controller. The auxiliary models can also be used to describe impacts on physiological characteristics such as blood pressure. Aspects of the invention facilitate both robust control and constrained control as a solution to the problem of providing effective and physiologically safe control for systems under significant inter-patient uncertainty.

An MPC controller incorporating an auxiliary model was presented for control of depth of hypnosis in adults and children. A first step involves designing an MPC controller. The control strategy associated with the MPC controller may be designed to overcome the large inter-patient variability in response to a standardized anesthetic drug infusion using robust control principles. First, a nominal model may be constructed from individual frequency responses of patient models. To reduce the uncertainty due to inter-patient variability, the parameters of the nominal model may be tuned by minimizing the difference between the nominal and individual patient models in the frequency domain. The uncertainty with respect to this nominal model may then be quantified. The effect of the tunable controller parameters on stability and performance may be investigated by using sensitivity functions. For each population, the performance of the MPC controller on a set of models may be assessed in simulation during induction and maintenance of anesthesia including surgical stimulation. Evaluation of the MPC controller showed that the MPC controller meets desired design specifications and achieves the required robustness against patient uncertainty.

Evaluations on the MPC controller according to the embodiments described herein were conducted for adults and children assuming that no constraints are active. The objectives of the evaluations were: (1) to design an MPC controller for adults ($MPC_{adult}$) that provides adequate propofol infusion for the complete study population, (2) to compare the $MPC_{adult}$ with previously published robust designs and check the feasibility of achieving similar performance with the new MPC controller, that can be extended to constrained and multivariable control, (3) to define a nominal model and uncertainty description in children, and (4) to design a robust MPC controller for children ($MPC_{child}$) that can meet clinical criteria.

Evaluations were also conducted on an MPC-based controller with the imposition of additional constraints on drug concentrations and/or physiological characteristics for closed-loop control of anesthesia drugs (such as propofol).

An auxiliary model was used to estimate or determine the drug concentration levels within a patient which were projected into the input space of the MPC controller when performing the MPC optimization. The objectives of the evaluations were: (1) to explore the importance of constraints in closed-loop control of hypnosis, (2) to add constraints to the previously designed and evaluated MPC controller, and (3) to assess the consequences of the constraints on the performance of the closed-loop control system in simulation. The MPC controller and methods described herein may incorporate constraints based on physiological characteristics, such as systolic blood pressure, and/or the like. The MPC-based systems and methods described herein may additionally or alternatively incorporate constraints based on other physiological characteristics.

An MPC controller according to various embodiments of the invention are discussed below as applied to closed-loop control of propofol (a hypnotic), with reference to the steps in designing, developing and evaluating the controller. As discussed below, a nominal model was first derived to model patients' response to propofol based on a measured or predicted output (for example, in this case, output from a depth of hypnosis (DOH) monitor which is indicative of a patient's depth of sedation or anesthesia). The uncertainty of the model, due to inter-patient variability, was then quantified with respect to the nominal patient model. An MPC controller was designed around the nominal model and its uncertainty. An auxiliary model was incorporated into the MPC controller to constrain the MPC controller based on drug concentration levels and/or physiological characteristics. Minimization of an MPC index was performed subject to these constraints. The physiological characteristics that are used to constrain the system may be determined from an auxiliary model, which may comprise a PKPD model, a population-based PKPD model, a patient-specific PKPD model (e.g. based on the patient's history), a multi-compartment PKPD model, a Kalman filter, and/or the like.

An auxiliary model may also be used to describe impacts of the propofol on other physiological characteristics such as blood pressure. In some embodiments, certain physiological characteristics (such as systolic blood pressure) may be measured from the patient and these measured physiological characteristics may be used with an auxiliary model to refine other physiological characteristics (such as drug concentration levels or the like) which are used to constrain the system. In other embodiments, an auxiliary model may be used to estimate values for physiological characteristics such as blood pressure and these values may then be used to predict drug concentration levels and/or other physiological characteristics which are used to constrain the system.

Particular embodiments of the MPC-based system and methods described herein may be used to control the delivery of anesthesia drugs to a patient during a clinical and/or surgical procedure. "Anesthesia drugs" (or equivalent terms), as used herein, may refer to any drug that may be used for the purposes of sedating the patient and/or temporarily inducing in the patient a state of anesthesia (which may incorporate one or more of analgesia, paralysis, amnesia and/or unconsciousness), and may comprise, among other drugs, analgesics, hypnotics, neuromuscular blocking agents, and/or the like.

Agents that may be administered to a patient in a controllable manner using the systems and methods described herein may be administered in any of a variety of known routes. Examples of methods that may be suitable for the administration of a drug agent or compound include intravenous, inhalation, intramuscular, subcutaneous, intraperitoneal and intrathecal delivery methods and the like. As a general reference, see for example, Remington, The Science and Practice of Pharmacy, Edited by Allen, Loyd V., Jr, 22nd edition, 2012, Pharmaceutical Press.

Steps for Designing, Developing and Evaluating a Closed-Loop Control System for Anesthesia Delivery Step 1: Model Set Used for the Controller Design and Simulation Hypnotic state can be measured or estimated using depth of hypnosis (DOH) monitors such as the bispectral index (BIS) or the wavelet-based index ($WAV_{CNS}$) (see Johansen, M. D. P. D. Jay W. and M. B. B. S. P. D. M. B. A. Peter S. Sebel (2000), "*Development and Clinical Application of Electroencephalographic Bispectrum Monitoring*", The Journal of the American Society of Anesthesiologists 93(5): 1336-1344). The $WAV_{CNS}$ index provided by the NeuroSENSE monitor (NeuroWave Systems, Cleveland Heights, USA) is used as a monitor for DOH in currently preferred embodiments. The NeuroSENSE monitor was developed specifically for closed-loop control; the dynamic behavior of this monitor is time-invariant and does not add additional computational delays (Zikov, T., S. Bibian, et al. (2006), "*Quantifying cortical activity during general anesthesia using wavelet analysis*", Biomedical Engineering, IEEE Transactions on 53(4): 617-632 ("Zikov, Bibian et al. 2006"). As known by those skilled in the art, the NeuroSENSE monitor measures physiological characteristics of a patient and returns a $WAV_{CNS}$ value in a range of [1,100] with 100 being fully alert and 1 being the opposite of fully alert. Optimal hypnosis levels during stable state of general anesthesia are typically between $WAV_{CNS}$ index of 40-60 (Agrawal, G., Bibian, S., Zikov, T. (2010), "*Recommended clinical range for wavCNS*", Society for Technology in Anesthesia Annual Meeting).

Patient Model—Pharmacological Modeling

One commonly used intravenous hypnotic is propofol, which produces a sedative-hypnotic effect in the central nervous system. The effect of propofol is traditionally modeled using pharmacokinetic (PK) and pharmacodynamic (PD) models. In the evaluation conducted by the inventors, the model set described by Dumont et al. (Dumont 2008) and the model set identified by van Heusden et al. (van Heusden, K., J. M. Ansermino, et al. (2013), "*Quantification of the Variability in Response to Propofol Administration in Children*," Biomedical Engineering, IEEE Transactions on 60(9): 2521-2529 (van Heusden, Ansermino et al. 2013) were used for adults and children respectively. The adult model set includes 44 models, identified from data from 18-60 year old adults with an American Society of Anesthesiologists (ASA) status of I or II. The mean (SD) age and weights were 36(12) years and 80(14) kg. The model set for children is identified from data from 47 children age 6-16 years, ASA I-II, requiring general anesthesia. The mean (SD) age and weights were 12(3) years and 44(16) kg. The adult models use the 3-compartment PK model of Schüttler (Schüttler, M. D. J. and M. S. H. Ihmsen (2000), "*Population Pharmacokinetics of Propofol: A Multicenter Study*", The Journal of the American Society of Anesthesiologists 92(3): 727-738 ("Schüttler and Ihmsen 2000") and pediatric models use the Paedfusor PK model (Absalom, A. and G. Kenny (2005), "'Paedfusor' pharmacokinetic data set," British Journal of Anaesthesia 95(1): 110) to predict the propofol plasma concentration ($C_p$) as a function of the infusion rate (u):

$$\begin{bmatrix} \dot{C}_1 \\ \dot{C}_2 \\ \dot{C}_3 \end{bmatrix} \begin{bmatrix} -(k_{10}+k_{12}+k_{13}) & k_{12} & k_{21} \\ k_{12} & -k_{21} & 0 \\ k_{13} & 0 & -k_{31} \end{bmatrix} \cdot \begin{bmatrix} C_1 \\ C_2 \\ C_3 \end{bmatrix} + \begin{bmatrix} 1/V_1 \\ 0 \\ 0 \end{bmatrix}. \quad (1)$$

$$u(t)C_p(t) = \begin{bmatrix} 1 & 0 & 0 \end{bmatrix} \cdot \begin{bmatrix} C_1 \\ C_2 \\ C_3 \end{bmatrix}$$

where $C_1$ is the central compartment and $C_2$ and $C_3$ are the peripheral compartments, $k_{10}$ is the central compartment elimination rate constant and $k_{12}$, $k_{13}$, $k_{21}$ and $k_{31}$ are the inter-compartmental rate constants and $V_1$ is the central compartment volume (Schüttler and Ihmsen 2000). The pharmacodynamics of propofol is represented by a linear time invariant (LTI) transfer function and a non-linear function. The relationship between the plasma site concentration $(C_p(s))$ and the propofol concentration at the effect site $(G_e(s))$ may be described in the Laplace domain by:

$$C_e(s) = \frac{k_d}{s+k_d} e^{-T_d s} C_p(s) \quad (2)$$

where $T_d$ is a transport delay and $k_d$ is the rate of propofol distribution from the central compartment to the effect site compartment.

The relation between the $C_e(s)$ and the clinical effect (E) is described by a sigmoidal function known as the Hill function:

$$E = \frac{C_e^\gamma}{EC_{50} + C_e^\gamma} \quad (3)$$

where $EC_{50}$ is the steady state propofol concentration associated with 50% of the full clinical effect and $\gamma$ is a Hill function parameter which determines the steepness of the curve.

The linearized PD model for induction phase of anesthesia may then be expressed as:

$$PD(s) = e^{T_d s} \frac{k_d}{s+k_d} \frac{1}{2 \cdot EC_{50}} \quad (4)$$

Patient Model—Dose-Response Model

The drug-response relationship of propofol can be expressed by combining the PK and PD models. The PK model in (1) can be rewritten as a zero-pole-gain transfer function:

$$PK(s) = K_{PK} \frac{(s+z_1)(s+z_2)}{(s+p_1)(s+p_2)(s+p_3)} \quad (5)$$

where $K_{PK}$ is a constant gain, and p and z represent the poles and zeros, respectively.

The linearized PKPD model may be obtained by combining the PK and PD: (4), (5).

$$PKPD(s) = e^{-T_d s} K \frac{(s+z_1)(s+z_2)}{(s+p_1)(s+p_2)(s+p_3)(s+p_4)} \quad (6)$$

where K is the overall PKPD(s) gain.

Patient Model—Nominal Model

MPC typically involves the use of a process model to predict the future output values. The performance of MPC is dependent on the quality of this process model and hence it is important to define the model and quantify the uncertainty around it. Following the approach presented by Dumont et al. (in Dumont 2008), the nominal model $PKPD_o$ ($T_{do}$, $K_o$, $z_{o1}$, $z_{o2}$, $p_{o1}$, $p_{o2}$, $p_{o3}$, $p_{o4}$) may be constructed from the individual frequency responses of all patients in the study based on equation (6). A summary of the nominal parameters is presented in Table 1. To minimize the uncertainty, the parameters of $PKPD_o$ are tuned by minimizing the difference between the patients and the nominal frequency response using:

$$\min_{PKPD_o} \sum_{p=1}^{n} |PKPD_p(j\omega) - PKPD_o(j\omega)|, \quad (7)$$

$$\text{s.t. } lb \leq \theta \leq ub$$

where n is the number of patients in the group and $\theta = (T_{do}, K_o, z_{1o}, z_{2o}, p_{1o}, p_{2o}, p_{3o}, p_{4o})$ represents the optimum parameters of the nominal model and $lb = \min(T_d, K, z_1, z_2, p_1, p_2, p_4)$ and $ub = \max(T_d, K, z_1, z_2, p_1, p_2, p_3, p_4)$ are the lower and upper bounds of $\theta$ respectively.

TABLE 1

Optimum identified nominal model parameters

| | $T_d$ s | K $10^{-4}$/mg · s$^{-1}$ | $z_{1o}$ $10^{-3}$ | $z_{2o}$ $10^{-5}$ | $p_{1o}$ $10^{-2}$ | $p_{2o}$ $10^{-3}$ | $p_{3o}$ $10^{-4}$ | $p_{4o}$ $10^{-5}$ |
|---|---|---|---|---|---|---|---|---|
| Adult | 17 | 1.8 | 1.5 | 3.7 | 2.5 | 6.7 | 2.7 | 1.9 |
| Child | 48 | 1.3 | 0.9 | 5.2 | 2.0 | 5.0 | 4.9 | 3.9 |

Step 2: Controller Design

The nominal model obtained after discretization can be represented as a state-space model, which is one type of non-limiting MPC formulation often used in the research literature (see Bemporad, A. and M. Moran (1999), *Robust model predictive control: A survey. Robustness in identification and control*, A. Garulli and A. Tesi, Springer London. 245: 207-226). Maciejowski et al. showed that for every transfer function formulation of an MPC there is an equivalent state-space formulation (see Maciejowski 2002):

$$x(k+1) = Ax(k) + Bu(k)$$

$$y(k) = Cx(k) \quad (8)$$

In the evaluation conducted by the inventors, the disturbance is assumed to act on the output and $\eta(k)$ was defined as the disturbed output and $y(k)$ represents the actual measured output (see Maciejowski 2002). The setup for closed-loop control system 10 for anesthesia delivery to a patient is shown as a block diagram in FIG. 1. The system 10 comprises a controller 12 for controlling the delivery of anesthesia drugs to a patient 14 and a DOH monitor 16 for monitoring the patient 14's depth of hypnosis. Controller 12 is an MPC controller connected to an infusion pump 13 which controls the pump to deliver the drug at a particular infusion rate into patient 14 to take the patient to a desired depth of hypnosis (DOH). In the setup, r(t) is the desired or reference DOH set by the anesthesiologist, u(t) is the infusion rate calculated by the controller 12, d(t) represent a disturbance, such as a stimulation from the surgical procedure being performed on the patient, and y(t) is the DOH output from the DOH monitor 16. To obtain offset-free tracking, the equation (8) MPC state space formulation was augmented by defining a new state vector, z(k) and an augmented state space formulation:

$$z = \begin{bmatrix} \Delta x(k+1) \\ \eta(k+1) \end{bmatrix} = \overbrace{\begin{bmatrix} A & 0 \\ CA & 1 \end{bmatrix}}^{A_s} \begin{bmatrix} \Delta x(k) \\ \eta(k) \end{bmatrix} + \overbrace{\begin{bmatrix} B \\ CB \end{bmatrix}}^{B_s} \Delta u(k) + \begin{bmatrix} 0 \\ 1 \end{bmatrix} w(k) \quad (9)$$

$$y(k) = \underbrace{[0 \ 1]}_{C_s} \begin{bmatrix} \Delta x(k) \\ \eta(k) \end{bmatrix} + v(k)$$

where ($A_s$, $B_s$, $C_s$) are the state-space matrices of the augmented formulation, $G_s$ of the augmented model, w(k) and v(k) are the output disturbance and white measurement noises.

The augmented state vector z cannot be measured and, consequently, in some embodiments, is estimated, using the one-step ahead steady-state Kalman filter. From the estimated state z, the predicted output y(k) is calculated. The output in a compact matrix form is $$Y = F\hat{z}(k_i) + \Phi \Delta U \quad (10)$$

where $\hat{x}$ is the estimated state, $\Delta U$, Y and F and matrix $\Phi$ are defined as follow:

$$\Delta U = [\Delta u(k) \ \Delta u(k+1) \ \dots \ \Delta u(k+n_c-1)]^T$$

$$Y = [y(k+1) \ \dots \ y(k+n_p|k_i)]^T$$

$$F = \begin{bmatrix} C_s A_s \\ C_s A_s^2 \\ \vdots \\ C_s A_s^{n_p} \end{bmatrix}$$

$$\Phi = \begin{bmatrix} C_s B_s & \dots & 0 \\ C_s A_s B_s & s & \dots & 0 \\ \vdots & & & \\ C_s A_s^{n_p-1} B_s & s & \dots & C_s A_s^{n_p-n_c} B_s \end{bmatrix}$$

where $n_c$, the control horizon, is the number of samples used to capture the future control trajectory and $n_p$, the prediction horizon is the length of the optimization window.

The control objective is to minimize a performance index (cost function) involving the difference between the given set-point DOH signal r(k) and the measured (e.g. $WAV_{CNS}$) DOH y(k) within a prediction horizon (see equations (11) below). In these evaluations, a constraint which may be used is on the amplitude of the drug (e.g. propofol) infusion rate or control variable u(k):

$$\min_{\Delta u(k)} \left[ \sum_i^{n_p} \|y(k) - r(k)\|_Q^2 + \sum_0^{n_c-1} \|\Delta u(k)\|_R^2 \right] \quad (11A)$$

$$\text{s.t. } u_{min} \leq u(k) \leq u_{max} \quad (11B)$$

where Q and R are weights of output error and changes to the infusion rate respectively.

Step 3: Determining the Robust Stability and Nominal Performance
Uncertainty Model Robustness may be defined with respect to PKPD model uncertainty and a fixed linear controller. Factors resulting in uncertainty in PKPD models include: age, weight, height, and medical history and/or the like, as individuals with different ages, weight, height, medical history, etc. may respond differently to the drug. This uncertainty in the frequency domain may be represented by multiplicative uncertainty, where the magnitude of the multiplicative uncertainty $I_1(\omega)$) may be expressed as:

$$l_I(\omega) = \max_{G_p \in \Pi} \left| \frac{G_p(j\omega) - G_o(j\omega)}{G_o(j\omega)} \right| \forall \omega \quad (12)$$

where $G_o$ is the nominal patient model with no uncertainty, $G_p$ is a particular patient model and $\Pi$ is the set of all patient models.
Sensitivity Functions Robustness to model uncertainties is reflected in the sensitivity function and the complementary sensitivity function based on the loop transfer function of the feedback system, L. The sensitivity functions are defined as:

Sensitivity function: $S = (1+L)^{-1}$

Complementary Sensitivity function: $T = L(1+L)^{-1}$ \quad (13)

Robust Stability (RS) and Nominal Performance (NP) are guaranteed if:

$$\begin{cases} RS \Leftrightarrow |T(j\omega)|\langle 1/|w_I| \ \forall \ \omega \\ NP \Leftrightarrow |S(jw)| \langle 1/|w_P| \ \forall \ \omega, \end{cases} \quad (14)$$

where $w_1$ is the multiplicative uncertainty weight and $w_P$ is the performance weight.

Figure 2:
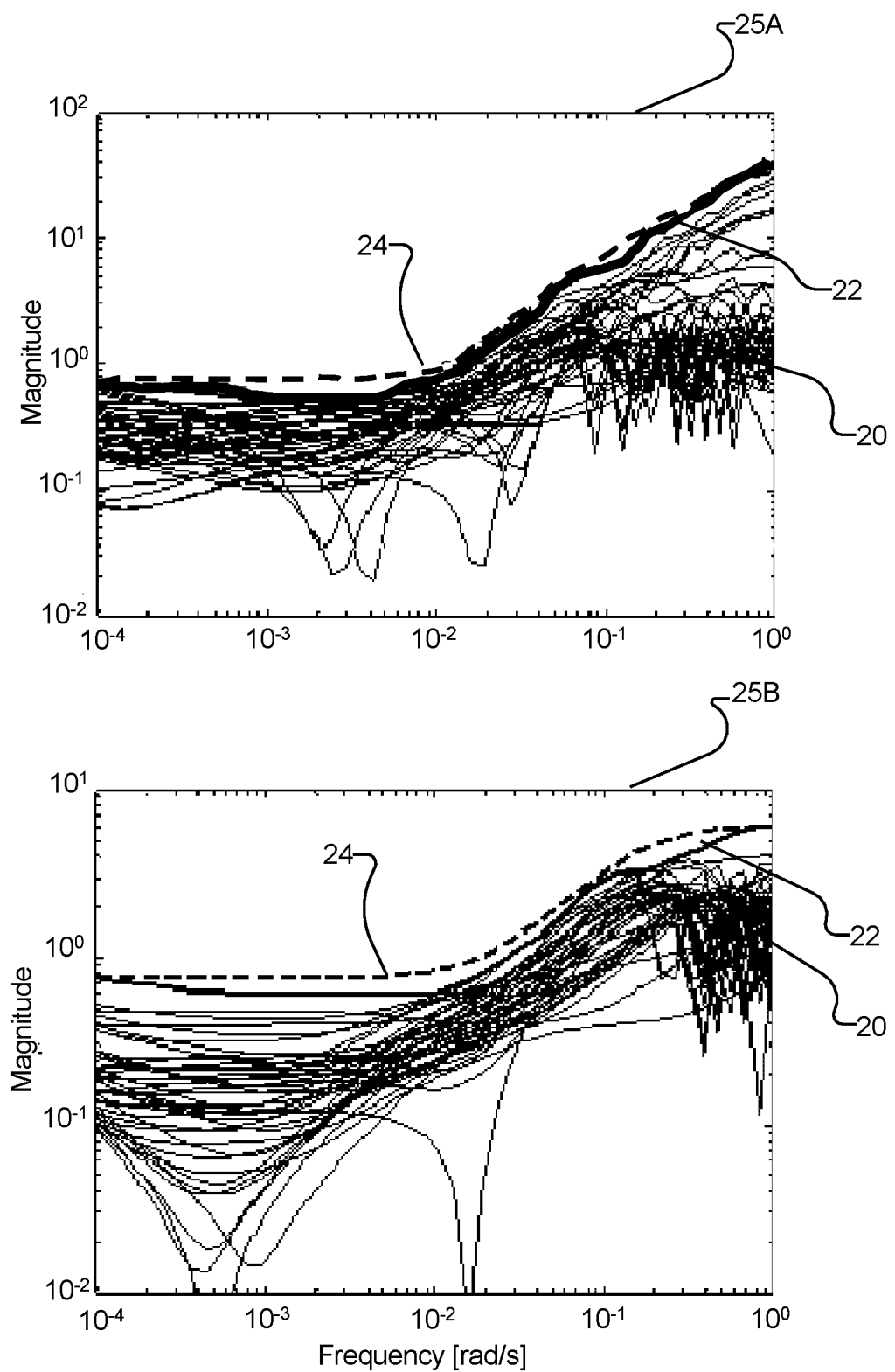
FIG. 2 illustrates the relative errors and uncertainty for samples of adults (A) and children (B).

The requirement of robust stability with multiplicative uncertainty gives an upper bound on T To represent unmodelled dynamics, $w_1$ may be determined by (Skogestad, S., Postlesthwaite, I. (2005), "*Multivariable feedback control: Analysis and Design,*" 2nd edition Wiley-Interscience ("Skogestad 2005")):

$$w_I(s) = \frac{\tau s + r_0}{(\tau/r_\infty)s + 1} \quad (15)$$

s.t. $|w_I(j\omega)| \geq l_I(\omega) \forall \omega$ where $r_0$ is the relative uncertainty at steady state, $1/\tau$ is approximately the frequency at which the relative uncertainty reaches 100%, and $r_\infty$ is the magnitude of the weight at high frequency (Skogestad 2005). FIG. 2 shows the relative errors for a sample of 44 adults (denoted as plot 25A) and 47 children (denoted as plot 25B) in solid lines 20 and the uncertainty, $I_1$ ($\omega$) (denoted by curve 22) and $w_1$ (denoted by curve 24) derived using the nominal model identified earlier.

To provide a clinically acceptable response, the system may be designed to have an overshoot of less than 15% and an initial rise time of less than 5 minutes. To meet the overshoot specification, the maximum value of the sensitivity function, $M_s$, may be limited to <2 (Astrom, K. J., Hagglund, T. (2006), Advanced PID Control; Research Triangle Park, N.C. ISA—The Instrumentation, Systems, and Automation Society). The weight $w_P$ is defined as an upper bound on the sensitivity S, based on $\omega_m$, the minimum bandwidth frequency, $E_S$ the maximum steady and $M_s$ state error and $M_s$ (Skogestad 2005):

$$w_P(s) = \frac{s/M_s + \omega_m}{s + \omega_m E_s}, \quad (16)$$

where $M_s = \max_\omega |S(j\omega)|$

The robust control theory considered here assumes that no constraints are active, so that evaluations can be conducted on the MPC controller operating in its unconstrained mode (i.e. as a linear controller), which is the case during most of the procedure (Maciejowski 2002), since even a constrained system should not hit its constraints too often when it is properly tuned and designed for its application.

Step 4: Robust Tuning of the Controller

Different tuning methods and formulations are available for designing a robust MPC (Mayne, D. Q., M. M. Seron, et al. (2005), "*Robust model predictive control of constrained linear systems with bounded disturbances*," Automatica 41(2): 219-224). An objective of the evaluation performed by the inventors was to determine an appropriate MPC tuning for automatic control of hypnosis.

The tuning parameters of the MPC controller $n_p$, $n_c$, and R, as well as the parameters for the Kalman filter may be tuned in a systematic way to meet the specifications defined in equation (14). In a first step, the Kalman filter parameters, and R may be tuned. This is achieved with a preliminary tuned MPC controller. The covariance of NeuroSENSE measurement noise is set to $R_v=9.0$ as described by Soltesz et al. (Soltesz, K., Van Heusden, K., Dumont, G. A., Hagglund, T., Petersen, C. L., West, N., Ansermino, J. M (2012), "*Closed-Loop Anesthesia in Children using a PID Controller: A Pilot Study*," IFAC conference on advances in PID control). Based on this particular $R_y$ value, the covariance $R_w$ may be identified to optimize the output predictive capability of the Kalman filter by minimizing the difference between the observed output from NeuroSENSE, $Y_{obs}$ and the predicted output from Kalman filter $Y_{est}$ such that robust stability and nominal performance holds:

$$\min_{R_w} \sum |y_{obs} - y_{est}| \quad (17)$$

In a second step, the MPC parameters may be tuned. Increasing $n_c$, increases the degree of freedom in calculating the control move. A longer control horizon, results in a faster system response at the cost of the system being less robust. Penalizing $\Delta u$ with R, results in a more robust controller at the price of the controller being sluggish (Varvel, J. R., D. L. Donoho, et al. (1992), "*Measuring the predictive performance of computer-controlled infusion pumps*", J Pharmacokinet Biopharm 20(1): 63-94 ("Varvel et al. 1992"). Altering $n_p$ concerns a trade-off between the rise-time and the overshoot upon induction of anesthesia. Increasing $n_p$ has a stabilizing effect but also increase the computational effort. The parameters were tuned to optimize performance while meeting the robustness criteria, according to the following algorithm ("MPC Tuning Algorithm"):

- initialize the preliminary MPC parameters
- fix $R_v$ value, and select $R_w$ by minimizing the difference between $Y_{obs}$ and $Y_{est}$ using Equation (17)
- for MPC parameter: { nc, R, Np}:
  - while conditions for Equation (14) are satisfied:
    - evaluate time-domain performance by calculating rise-time and overshoot values
    - evaluate $M_s$
    - select the parameter which results in lowest $M_s$ value when rise-time and overshoot specifications (Robust Stability and Nominal Performance Sensitivity Functions) are met
  - end
- end .

For the example preliminary tuned controller developed by the inventors, the prediction horizon was fixed to $n_p=60$ samples, corresponding to the 5 minutes induction time with sampling time of $t_s=5$ seconds. The remaining MPC parameters were chosen as $n_c=1$, and R=1. Minimization for Kalman filter tuning was performed with values in the range 0.01-10, where predictability of the filter improved with increasing value of $R_w$. With $R_v$ values fixed to 9.0, increasing $R_w$, increased the observer gain meaning that for a noisy output, the gain will amplify the noise in the output. $R_w$ was set to 1 to provide accurate predictions, while keeping the observer gain small.

Figure 3A:
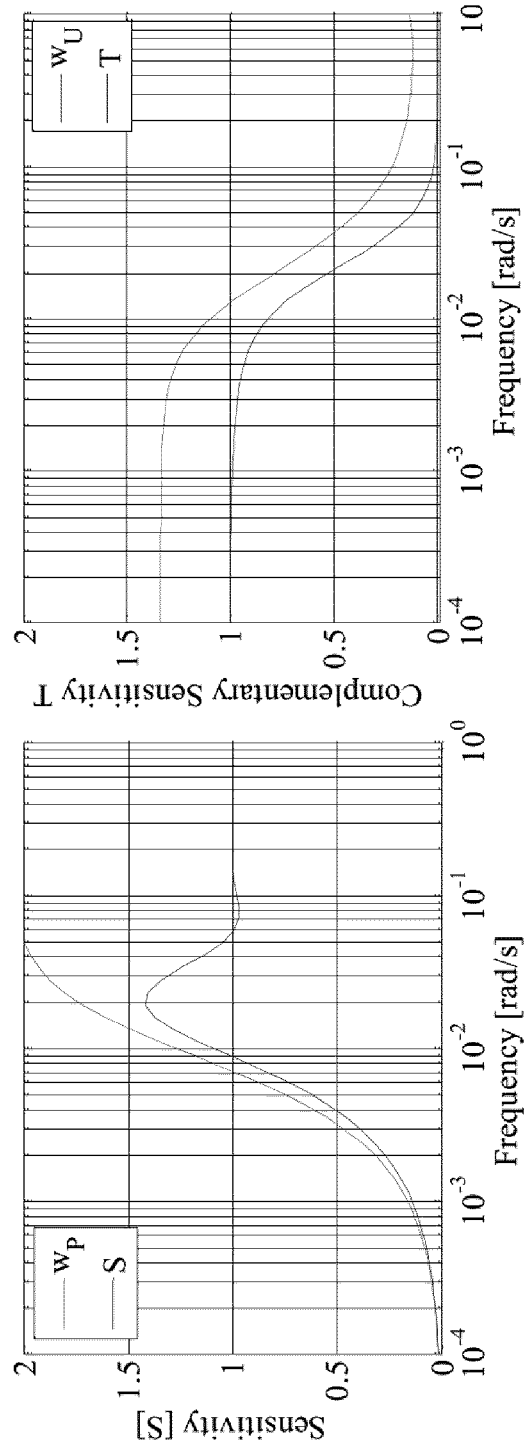
FIG. 3A and FIG. 3B illustrate a closed-loop sensitivity and complementary sensitivity analysis for the nominal system for samples of adults (A) and children (B).
Figure 3B:
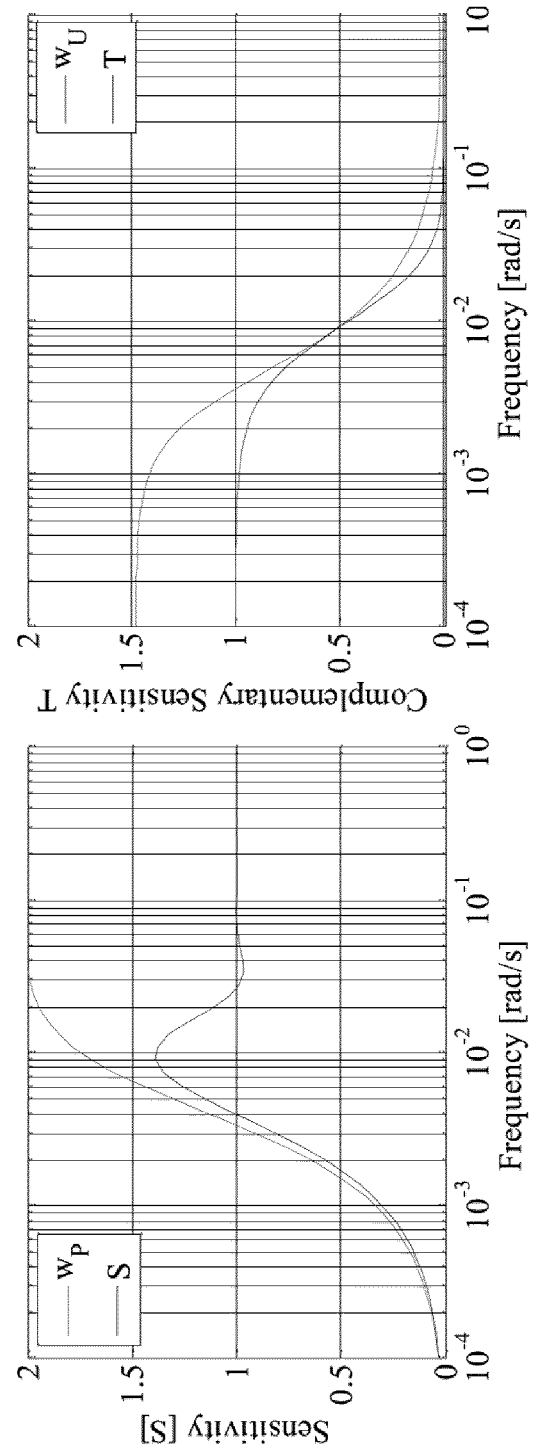

MPC parameter tuning started with $n_c$. Increasing the control horizon to $n_c=2$ resulted in a faster rise-time. The system remained stable and the added computational cost was negligible. For $n_c$ values greater than 2, the nominal system was unstable. The effect of changing R was examined for values between 0.1-1. The controller attained robust stability and nominal performance with all the values in the range. For R value 0.3, the system achieved a fast induction with no initial overshoot. With $n_c=2$, =1, $R_v=9$, R=0.3, $n_p$ values between 40 to 100 were considered. The controller achieved robust stability and nominal performance for all $n_p$ values in the specified range. The prediction horizon, $n_p$ was fixed at 70, as the system achieves the smallest $M_s$ value with that tuning parameter. This manually tuned controller satisfies the robust stability requirement and the nominal performance requirement as shown in FIG. 3A Following the MPC Tuning Algorithm and the same tuning guideline described for adults, the MPC controller for children is tuned with parameters set to $n_c=2$, $R_w=0.01$, $R_v=9$, R=0.3, $n_p=50$. The robust stability and nominal performance conditions and the sensitivity plots are presented in FIG. 3B.

Step 5: Closed-Loop Simulations

Simulation Set-Up

For each (e.g. adult and children) controller, a 60 minute surgical procedure was simulated for the complete set of models assuming an infusion rate of 10 mg/ml propofol. Simulations were performed using nonlinear patient models. The target DOH was set to a $WAV_{CNS}$ 50 for the duration of the procedure. For all patients, a hypothetical surgical stimulus was fixed to start 20 minutes after the beginning of the simulation. This stimulus profile was adapted from Dumont 2008. The infusion rate in this study is constrained between $u_{min}=0$ and $u_{max}=1200$ ml/hr which is the maximum infusion rate of the propofol pump.

Closed Loop Responses

For assessment of the adult MPC controller, results were compared to the results from the controller by Hahn et al. (Jin-Oh, H., G. A. Dumont, et al. (2010), Robust closed-loop control of propofol administration using $WAV_{CNS}$ index as the controlled variable, Engineering in Medicine and Biology Society (EMBC), 2010 Annual International Conference of the IEEE ("Hahn, Dumont, et al. 2010"). The nominal model in both designs was constructed from the PK model by Schüttler and characteristic data and PD parameters from Dumont 2008. For Hahn et al., the controller was also fixed for all patients and the patient models were divided into four age groups (Gr 1:18-30 yr, Gr 2:31-40 yr, Gr 3: 41-50 yr, and Gr 4:51-60 yr) to also investigate the effect of age as a covariate.

Results from the MPC controller for children were compared with the results from the clinical evaluation of a PID controller in van Heusden et al. 2014. The controller in both designs use the Paedfusor PK model and PD parameters from van Heusden, Ansermino et al. 2013. In the van Heusden et al. study, anesthesia was closed-loop controlled in 102 children ASA I-II where median (range) age and weights were 12.5(6-17) yr and 48(19-75) kg. The study was conducted in two stages. The originally tuned PID controller was evaluated in 31 cases.

The acquired results were used to fine tune the final controller which was evaluated in 71 cases. The controller performance at induction (0 min<time <20 min) of anesthesia was evaluated based on overshoot, $S_{os}$ and with rise-time, $T_{ind}$. During maintenance (20 min <time <60 min) of anesthesia, the performance of the MPC controller was assessed in terms of percentage error (PE)-based metrics commonly used in anesthesia closed-loop control systems (Varvel et al. 1992). The median PE (MDPE), median absolute PE (MDAPE), divergence and wobble were calculated using the maintenance portion of the procedure and are presented in Table 2 and Table 3 respectively. The sign of MDPE represents the direction of the PE, where a negative value indicates that the controller tends to overdose the patient, leading to DOH levels below target, whereas a positive value shows the tendency of a light anesthesia. MDAPE indicates the expected size of the error between the systems output and the set-point. Wobble measures the intra-patient variability in performance errors and divergence reflects the possible time-related trend of the output in relation to the set point. (PE)-based metrics were introduced to assess the performance of target controlled infusion (TCI) systems. These metrics are argued to be inadequate for evaluating EEG-guided automatic control of depth of hypnosis (Soltesz, K., G. A. Dumont, et al. (2013), Assessing control performance in closed-loop anesthesia, Control & Automation (MED), 2013 21st Mediterranean Conference on) and were only employed in these preliminary evaluations to provide a comparison of current results and those obtained in Hahn, Dumont et al. 2010 and in van Heusden et al. 2014.

TABLE 2

Performance of the MPC and the Hahn et al. controller (Hahn, Dumont et al. 2010) during induction and maintenance of simulated surgery in adults.
Group[age interval]: 1: [18-30] yr, 2: [31-40] yr, 3: [41-50] yr, 4: [51-60] yr.

| Group | Number | Controller | $S_{os}$ [%] | $T_{ind}$ $WAV_{CNS} < 55$ [min] | MDPE [%] | MDAPE [%] | Divergence [%/min] | Wobble [%] |
|---|---|---|---|---|---|---|---|---|
| All | 44 | $MPC_{adult}$ | 3.7 ± 7.5 | 4.1 ± 2.1 | — | 0.9 ± 0.8 | −0.02 ± 0.01 | 0.9 ± 0.8 |
| 1 | 15 | MPC | 7.6 ± 10.5 | 3.4 ± 1.2 | — | 0.6 ± 0.6 | −0.02 ± 0.01 | 0.5 ± 0.5 |
|   |   | Hahn | 14.3 ± 9.8 | 5.2± | 0.1 ± 0.4 | 2.9 ± 1.1 | −0.26 ± 0.10 | 2.9 ± 1.1 |
| 2 | 12 | MPC | 2.6 ± 6.3 | 3.7 ± 1.3 | — | 0.7 ± 0.3 | −0.02 ± 0.01 | 0.6 ± 0.2 |
|   |   | Hahn | 13.7 ± 12.8 | 2.4 ± 0.3 | 1.2 ± 0.2 | 1.6 ± 0.3 | −0.09 ± 0.03 | 0.6 ± 0.2 |
| 3 | 8 | MPC | 0.61 ± 1.72 | 5.3 ± 2.3 | — | 1.5 ± 1.4 | −0.02 ± 0.01 | 1.5 ± 1.5 |
|   |   | Hahn | 15.1 ± 4.3 | 2.8 ± 0.2 | 0.9 ± 0.2 | 1.5 ± 0.3 | −0.10 ± 0.03 | 1.0 ± 0.3 |
| 4 | 9 | MPC | 1.4 ± 3.1 | 4.7 ± 2.1 | — | 1.2 ± 0.8 | −0.02 ± 0.01 | 1.1 ± 0.8 |
|   |   | Hahn | 2.0 ± 5.0 | 5.3 ± 1.3 | 0.5 ± 0.3 | 2.6 ± 0.7 | −0.28 ± 0.08 | 2.8 ± 0.7 |

TABLE 3

Performance of the MPC and the van Heusden et al. controller (van Heusden et al. 2014) during induction and maintenance of simulated surgery in children.

| Number | Controller | $S_{os}$ [%] | $S_{os}$ 3 min after $T_{ind}$ [index] | $T_{ind}$ $WAV_{CNS} < 60$ [min] | MDPE [%] | MDAPE [%] | Divergence [%/min] | Wobble [%] |
|---|---|---|---|---|---|---|---|---|
| 47 | $MPC_{child}$ | 7.3 ± 7.8 | 50 ± 5 | 5.0 ± 1.8 | −3.6 ± 1.3 | 5.3 ± 1.7 | −0.04 ± 0.1 | 4.0 ± 1.4 |
| 31 | van Heusden | N/A | 40 ± 5 | 4.5 ± 1.5 | −8.7 ± 7.8 | 11.5 ± 6.3 | N/A | 6.2 ± 3.5 |
| 71 | van Heusden | N/A | 42 ± 5 | 3.7 ± 1.2 | −6.2 ± 5.3 | 8.8 ± 4.2 | N/A | 6.0 ± 2.4 |

These evaluations determined that the example MPC controllers described herein met the overshoot specification. $WAV_{CNS}$ values below 40 are associated with occurrence of apnea making the overshoot value a significant performance factor, especially for the cases where spontaneous breathing is required. Pain on injection of propofol is another common concern particularly for pediatric anesthesiologists, making the rise-time another important aspect in performance evaluation for closed-loop control of anesthesia. In the field of anesthesia, rise-time is commonly defined as the time that takes for DOH index to fall below 60 and for the patient to be in a moderate hypnotic state. A $WAV_{CNS}$ index of 60 was reached with the $MPC_{adult}$ and $MPC_{child}$ controllers within an average of 4.1 min and 5 min respectively. The trade-off to guarantee stability given the large inter-patient variability is the slower than desired rise-time for insensitive patients.

Figure 4:
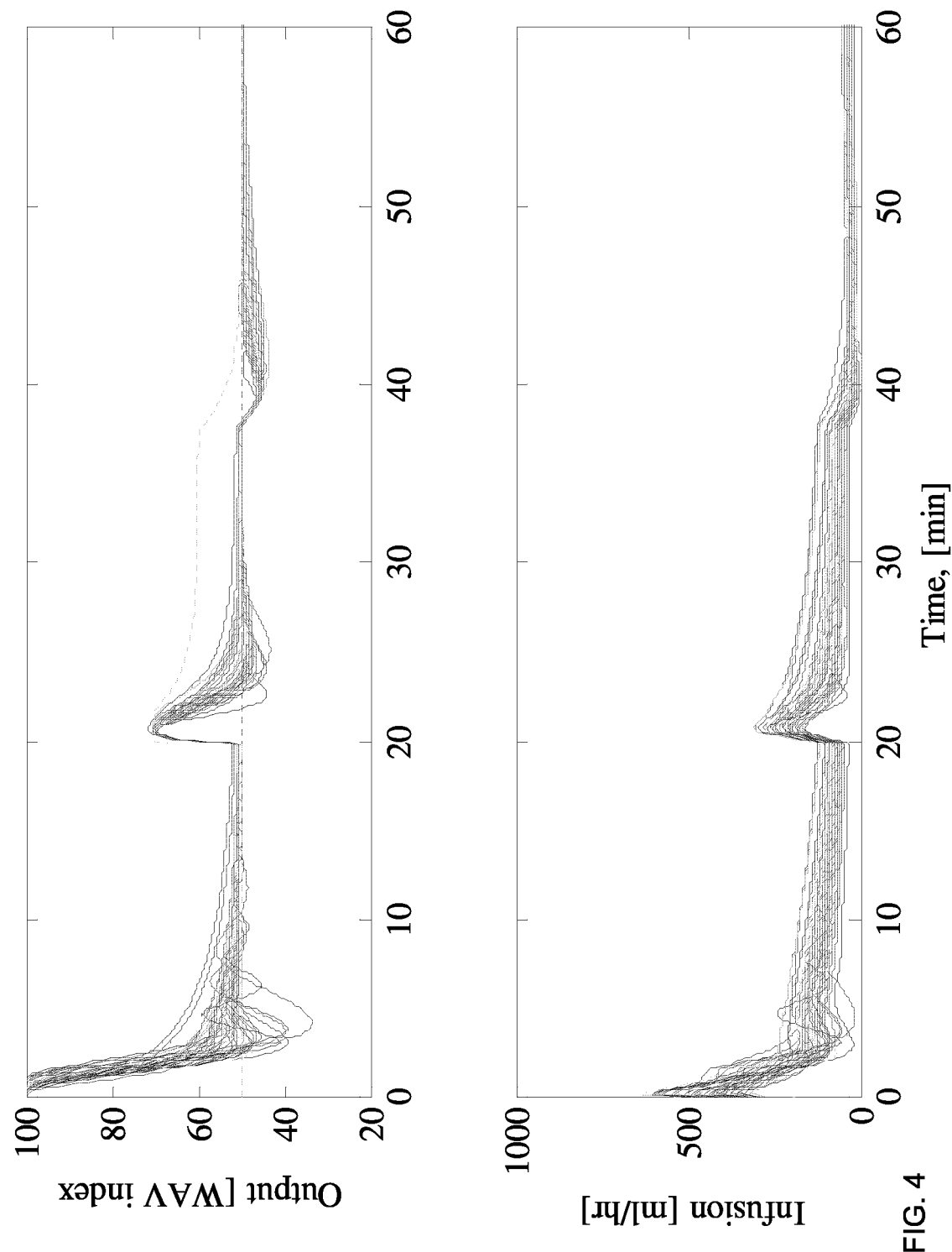
FIG. 4 illustrates a closed-loop $MPC_{adult}$ control response of 44 patient models using $WAV_{CNS}$ index wherein a hypothetical surgical stimulus is fixed to start 20 minutes after the beginning of the simulation (shown as the dotted line).
Figure 5:
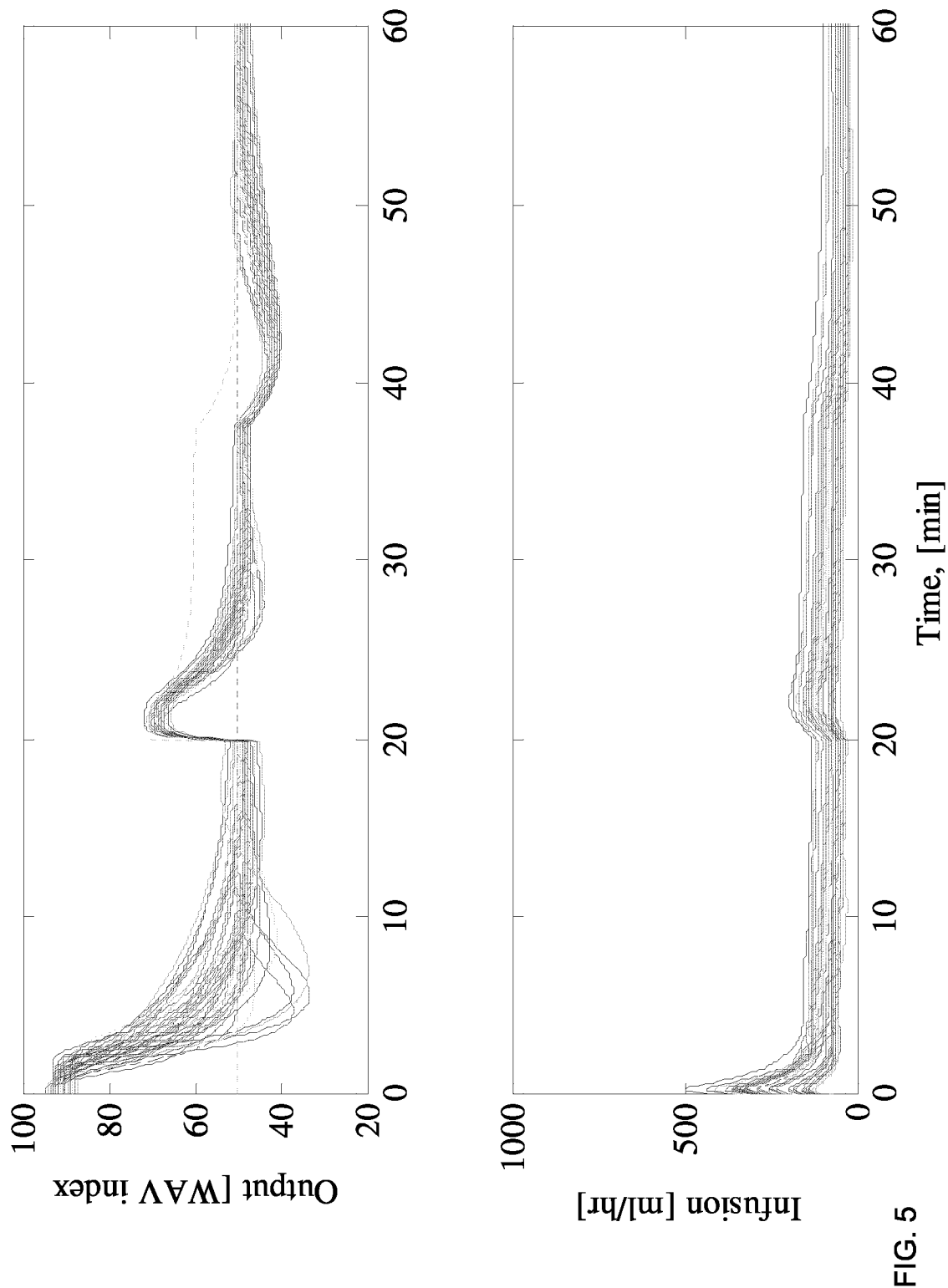
FIG. 5 illustrates a closed-loop $MPC_{child}$ control response of 47 patient models using $WAV_{CNS}$ index wherein a hypothetical surgical stimulus is fixed to start 20 minutes after the beginning of the simulation (shown as the dotted line).

FIGS. 4 and 5 show the MPC closed-loop simulations for the 44 adult patients and 47 pediatric patients respectively. The results show that despite the large inter-patient variability in adults and especially in children, stability and performance was achieved. Evaluation of the proposed MPC controllers during simulated induction and maintenance of anesthesia show that the design specifications are met and that the desired robustness against patient uncertainty was achieved.

Step 6: Addition of Safety Constraints to the MPC Controller Using an Auxiliary Model Constraints on the amplitude of the control variable u, which, in the examples described herein, is the propofol infusion rate, may arise from the hard physical constraints on the system. By way of non-limiting example, such hard physical constraints may include that the infusion rate cannot be negative, and the infusion rate must be less than the maximum rate that can be provided by the infusion pump. In addition to or in the alternative to hard physical constraints, constraints can also be applied on other criteria (e.g. patient safety and/or the like). For example, in the control of propofol administration, constraints can be enforced to minimize hemodynamic changes which tend to follow propofol delivery to the patient. Bilotta et al. showed in a study in which patients were randomly assigned to receive propofol at two different infusion rates (10 mg/s vs 2 mg/s), that the higher infusion rate induced a larger drop in mean arterial pressure than the lower infusion rate (Bilotta, F., L. Fiorani, et al. (2001), "*Cardiovascular effects of intravenous propofol administered at two infusion rates: a transthoracic echocardiographic study*," Anaesthesia 56(3): 266-271). Having constraints on the magnitude of u may give the option to limit the maximum infusion rate. The infusion rate in the example evaluations conducted by the inventors was constrained between 0 and 600 ml/hr, whereas the infusion pump is capable of 1200 ml/hr.

$$0 \leq u(t) \leq 600 \text{ ml/hr} \quad (18)$$

One of the main effects of propofol on the cardiovascular system is a decrease in arterial blood pressure due to a drop in systemic vascular resistance. Reductions in systolic blood pressure (SBP) greater than 25% have been reported during induction of anesthesia with propofol (Kazama, T., K. Ikeda, et al. (1999), "*Comparison of the effect-site k(eO)s of propofol for blood pressure and EEG bispectral index in elderly and younger patients*," Anesthesiology 90(6): 1517-1527 ("Kazama, Ikeda et al. 1999")). West et al. (West, N. V. H., K., Gorges, M., Petersen, C. L., Umedaly, A., Dumont, G. A., Ansermino, J. M. and Merchant, R. N (2014), "*Blood pressure changes during closed-loop control of anesthesia*," Proceedings of the Canadian Anesthesiologists Society Annual Meeting) evaluated the intraoperative blood pressure measurements for 35 adults age 64.5 [38-81] yr, ASA I-III where propofol was closed-loop controlled and remifentanil was administered by target controlled infusion. Hypotension was treated in 7 (19/%) subjects during the period between start of propofol infusion and incision. Kazama et al., investigated the effect of age on SBP change with propofol in patients aged 20-85 yr. Their results showed that at high plasma concentrations (>10 µg/ml), propofol may significantly decrease SBP, an effect more evident in elderly (>70 yr) patients (Kazama, Ikeda et al. 1999).

Another effect of propofol at high concentration is a reduction of cerebral electrical activity as confirmed by an electroencephalography (EEG) Burst Suppression (BS) pattern with significant periods of isoelectric activity (Illievich, U. M., W. Petricek, et al. (1993), "*Electroencephalographic burst suppression by propofol infusion in humans: hemodynamic consequences*," Anesth Analg 77(1): 155-160 ("Illievich, Petricek et al. 1993"). Besch et al reported that the occurrence of isoelectric periods is more frequent with increasing hypnotic drug concentration, suggesting that BS may indicate too deep anesthesia (Besch, G., N. Liu, et al. (2011), "*Occurrence of and risk factors for electroencephalogram burst suppression during propofol-remifentanil anaesthesia*," Br J Anaesth 107(5): 749-756). Their study concluded that the main independent factors linked with BS were advanced age, medical history of coronary disease and male gender. BS onset has been reported with effect-site concentrations higher than 8 µg/ml (Illievich, Petricek et al. 1993) without opioids and 7.3 µg/ml with an opioid (remifentanil 30 µg/kg/min).

The lower bound on the propofol concentration may be generally defined by concentrations which admit patient awakening. Light anesthesia is a result of low propofol concentration and is associated with an increased possibility of awareness during surgery (Ghoneim, M. M., R. I. Block, et al. (2009), "*Awareness during anesthesia: risk factors, causes and sequelae: a review of reported cases in the literature*," Anesth Analg 108(2): 527-535.). Propofol concentrations less than 1.6 m/ml (when administered with fentanyl) (Kazama, Ikeda et al. 1999) and 1.8 µg/ml (Iwakiri, H., N. Nishihara, et al. (2005), "*Individual effect-site concentrations of propofol are similar at loss of consciousness and at awakening*," Anesth Analg 100(1): 107-110) without opioids are associated with awakening from anesthesia.

To place safety bounds or constraints on the dosage of the drug, values with respect to a therapeutic window of the drug may be used to define drug concentration levels in the patient's body, and side effects may be minimized or reduced by staying within the therapeutic window. Thus, safety bounds on the estimated propofol plasma concentration ($C_p$) and estimated effect-site concentration ($C_e$) can be defined using the therapeutic window for propofol as constraints on measured physiological characteristics explained above. In particular embodiments, the following bounds may be used in the controller design:

$$1.6 \leq C_p \leq 10 \text{ µg/ml} \quad (19)$$

$$1.6 \leq C_e \leq 7 \text{ µg/ml} \quad (20)$$

It should be noted that the concentrations expressed in equations (19) and (20) are based on an open-loop population-based PKPD model and thus may not be an optimal indication of the actual concentrations for a particular patient. This reinforces the desirability of incorporating constraints on measured physiological characteristics.

Patient Model

The effect of propofol is traditionally modelled using pharmacokinetic (PK) and pharmacodynamics (PD) models. PK models are used to estimate the plasma drug concentration profile of a drug in response to its administration. The plasma concentration of a drug in a patient may be referred to as $C_p$. PD models can be employed to estimate the drug concentration at a hypothetical effect-site (often referred to as $C_e$) with an equilibrium constant ($k_{e0}$) describing the dynamic delay associated with the distribution of the drug between the plasma and the effect-site. PD models may also describe the relationship between the concentration of the drug at the effect-site and the clinical effect of the drug.

In some embodiments, the dose-response relationship of propofol could be expressed by using a PKPD model. However, in currently preferred embodiments, a nominal model, Go, is employed. $G_o$ is based on a model set described by Dumont et al. (Dumont 2008). The set includes 44 models, identified from 18-60 year old adults with an American Society of Anaesthesiologist (ASA) status of I or II. The mean (SD) age and weights were 36(12) years old and 80(14) kg. In some embodiments, the nominal model Go, in state-space formulation, may be used in the controller.

$$x(k+1)=Ax(k)+Bu(k)$$

$$y(k)=Cx(k) \quad (21)$$

Controller Set-Up Based on Nominal Model

FIG. 1B shows a closed-loop control system 10 for delivery of a drug (in this example embodiment, an anesthesia drug, in particular, propofol) to a patient according to a particular example embodiment. It will be appreciated from the description that follows that control system 10 and its components could be suitably modified to controllably deliver other drugs. Control system 10 and in particular controller 12 are based on an MPC control scheme based on a nominal model Go. System 10 comprises an MPC controller 12 for controlling the delivery of an anesthesia drug (e.g. propofol) to patient 14 and a DOH monitor 16 for monitoring the depth of hypnosis (DOH) of patient 14. DOH monitor 16 may comprise an electroencephalogram (EEG) monitor, wherein physiological EEG data from sensors placed on the forehead may be used to assess the patient's DOH. The DOH output from the monitor 16 can be represented, for example, as a $WAV_{CNS}$ index ranging from 0 for iso-electric EEG to 90-100 for full consciousness. It will be appreciated that DOH monitor 16 is an example of a monitor that is useful for sensing the physiological characteristics of patient 14 and determining therefrom a monitor measurement that is useful for the cases where the drug being administered is propofol and/or some other anesthetic drug. In general, however, where control system 10 is used for different types of drugs, monitor 16 need not be a DOH monitor. Instead, monitor 16 may generally comprise any suitable device which senses one or more monitorable physiological characteristics of patient 14 and which determines therefrom one or more monitor measurements indicative of the effect of the drug being administered on the patient. In system 10, controller 12 comprises a computer or a control and processing unit which is connected to a source of the drug to be administered (not shown in FIG. 1) and to a controllable drug administration actuator 13. In the case of the illustrated embodiments, drug administration actuator 13 comprises a controllable infusion pump or infusion syringe 13.

Controller 12 is configured to determine one or more control variables u(t), also referred to as control signal u(t) and/or manipulated variables u(t), which may in turn be used to control drug administration actuator 13. In the particular case where drug administration actuator 13 comprises an infusion pump, control signal u(t) may be considered to comprise or be otherwise correlated with an infusion rate u(t) of the drug being administered. In the case of the example embodiment of FIG. 1, controller 12 determines a control variable which is used to generate a control signal which in turn is used to control syringe pump 13 to deliver propofol at a particular infusion rate. In the exemplary control system 10 of FIG. 1, r(t) is a desired or reference level (also referred to as a set point) for the monitor measurement. For example, in the exemplary embodiment where the drug being administered is propofol and monitor 16 is a DOH monitor, r(t) may be a reference DOH level, which may be set by an anesthesiologist, for example. When the drug is administered to patient 14 via drug administration actuator 13, the response of patient 14 is monitored by monitor 16 (DOH monitor 16, in the case of the FIG. 1 example embodiment) and monitor 16 generates a corresponding monitor measurement y(t). The monitor measurement y(t) may be referred to as the controlled variable. Control system 10, an in particular controller 12 uses reference level r(t) and the monitor measurement y(t) from monitor 16 to calculate a control signal u(t) which will cause monitor measurement y(t) to track reference level r(t). Where controller 12 implements a digital MPC based control scheme (as is the case in the illustrated embodiment), controller 12 may determine a control signal u(t) in each of a series of time steps by minimizing a corresponding cost function (also referred to as optimizing a corresponding performance index) in each time step. The control signal u(t) determined by the optimization in each time step may be applied to drug administration actuator 13 in a subsequent time step.

To obtain offset-free tracking for the case of the example FIG. 1 embodiment, controller 12 of the exemplary FIG. 1 embodiment may incorporate the nominal model $G_o$ in the augmented formulation (van Heusden et al. 2014) described above, where η(k) is defined as the disturbed output and y(k) represents the actual monitor measurement output (Maciejowski 2002). In a discrete-time state-space formulation, this augmented controller formulation may be described by $$\begin{bmatrix} \Delta x(k+1) \\ \eta(k+1) \end{bmatrix} = \overbrace{\begin{bmatrix} A & 0 \\ CA & 1 \end{bmatrix}}^{A_s} \begin{bmatrix} \Delta x(k) \\ \eta(k) \end{bmatrix} + \overbrace{\begin{bmatrix} B \\ CB \end{bmatrix}}^{B_s} \Delta u(k) + \begin{bmatrix} 0 \\ 1 \end{bmatrix} w(k) \quad (22)$$

$$y(k) = \underbrace{[0,\ 1]}_{C_s} \begin{bmatrix} \Delta x(k) \\ \eta(k) \end{bmatrix} + v(k)$$

where ($A_s$, $B_s$, $C_s$) is the state-space representation of the augmented model, w(k) and v(k) are the output disturbance and white measurement noises respectively.

The augmented state vector $$\begin{bmatrix} \Delta x(k) \\ \eta(k) \end{bmatrix}$$

of the augmented nominal model cannot be measured and may therefore be estimated, using, for example, the one-step ahead steady-state Kalman filter.

Addition of Constraints Based on Auxiliary Model

Figure 6:
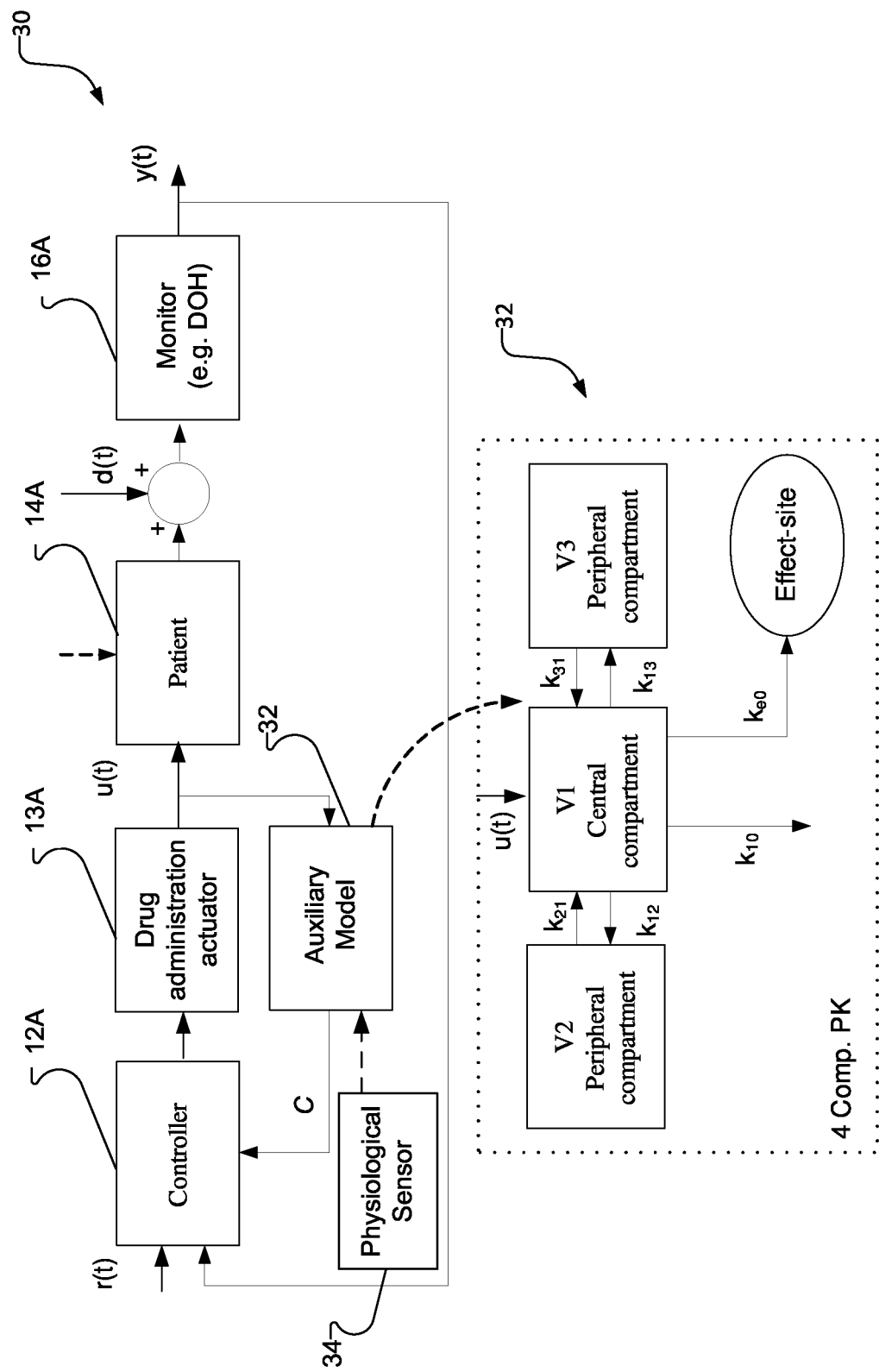
FIG. 6 illustrates a closed-loop system with a parallel 4-compartment PKPD model according to one embodiment wherein $k_{10}$ is the elimination rate, $k_{ij}$ is the distribution rate constant from compartment i to j. $k_{e0}$ is the plasma and effect-site equilibrium constant. $V_i$ is the volume of the compartment i.

As discussed above, the nominal model, $G_o$ used for the FIG. 1 control system 10 was constructed from individual frequency responses of a set comprising 44 subjects. Because of the frequency domain technique used in the construction of $G_o$, the states of the resulting controller do not represent hypothetical PK compartments. In particular, a nominal model constructed according to the above-described frequency domain techniques loses its PKPD structure and the states no longer represent drug concentrations. According to particular embodiments of the invention, an auxiliary model is added to the FIG. 1 control system 10, wherein the auxiliary model takes into account the control signal u(t) and estimates, based on the control signal u(t), at least one concentration level of the drug in the patient. FIG. 6 shows a control system 30 for closed loop control of administration of a drug (in the exemplary case, an anesthesia drug, particularly propofol) wherein an auxiliary model 32 is added to the FIG. 1 control system 10. In control system 30 shown in FIG. 6, drug administration actuator 13A and monitor 16A may be substantially similar to drug administrator actuator 13 and monitor 16 described herein in connection with control system 10 (FIG. 1). Except where otherwise indicated herein, controller 12A of the FIG. 6 control system 30 may be similar to controller 12 of the FIG. 1 control system 10.

As can be seen from FIG. 6, auxiliary model 32 receives control signal u(t) as input and uses control signal u(t) to estimate at least one concentration C of the drug in the body of patient 14. In some embodiments, the at least one concentration C comprises a plasma concentration G of the drug. In some embodiments, other concentrations such as a notional effect site concentration $C_e$ may be additionally or alternatively estimated by auxiliary model 32.

Controller 12A may implement a MPC control scheme which involves, for each of a series of time steps, minimizing a cost function (optimizing a performance index) which yields the control signal u(t) for the next time step. When auxiliary model 32 is incorporated into control system 30, the minimization performed by controller 12A at each time step may be subject to one or more constraints, wherein at least one such constraint is based on a concentration C estimated by auxiliary model 32. In some embodiments, as described in more detail below, auxiliary model 32 models the effect of the drug being administered on a physiological characteristic of the patient and may be used to map a constraint on the physiological characteristic into a corresponding constraint on an estimated concentration C that is output by auxiliary model 32 and provided to controller 12A.

In accordance with the particular example control system embodiment 30 shown in FIG. 6, auxiliary model 32 comprises a multiple-compartment PKPD model, e.g. a 4-compartment PKPD model (a 3-compartment PK model plus an effect-site compartment). As discussed above, auxiliary model 32 of the FIG. 6 example embodiment estimates the propofol concentration in a central compartment (referred to as a plasma concentration $C_p$) and an effective concentration at the effect-site (referred to as an effect site concentration $C_e$). The 4-compartment PKPD model 32 of the FIG. 6 example embodiment may be represented in state-space as follows:

$$\begin{bmatrix} \dot{x}_1 \\ \dot{x}_2 \\ \dot{x}_3 \\ \dot{x}_4 \end{bmatrix} = \underbrace{\begin{bmatrix} -(k_{10}+k_{12}+k_{13}+k_{e0}) & k_{12} & k_{13} & k_{e0} \\ k_{21} & -k_{21} & 0 & 0 \\ k_{31} & 0 & -k_{31} & 0 \\ k_{e0} & 0 & 0 & -k_{e0} \end{bmatrix}}_{A} \begin{bmatrix} x_1 \\ x_2 \\ x_3 \\ x_4 \end{bmatrix} + \underbrace{\begin{bmatrix} 1 \\ 0 \\ 0 \\ 0 \end{bmatrix}}_{B} u \quad (23)$$

where $k_{10}$ is the elimination rate, $k_{ij}$ is a distribution rate constant from compartment i to compartment j, $x_1$ represents the amount of drug in the central compartment, $C_p$, and $x_4$ represents the amount of drug in the effect-site compartment, $C_e$. By adding an auxiliary model 32 such as the 4-compartment PKPD model of equation (23) to an MPC controller, values for the concentrations $C_p$, $C_e$ can be determined and minimization of the MPC cost function can be carried out subject to constraints on these concentrations $C_p$, $C_e$.

Figure 7:
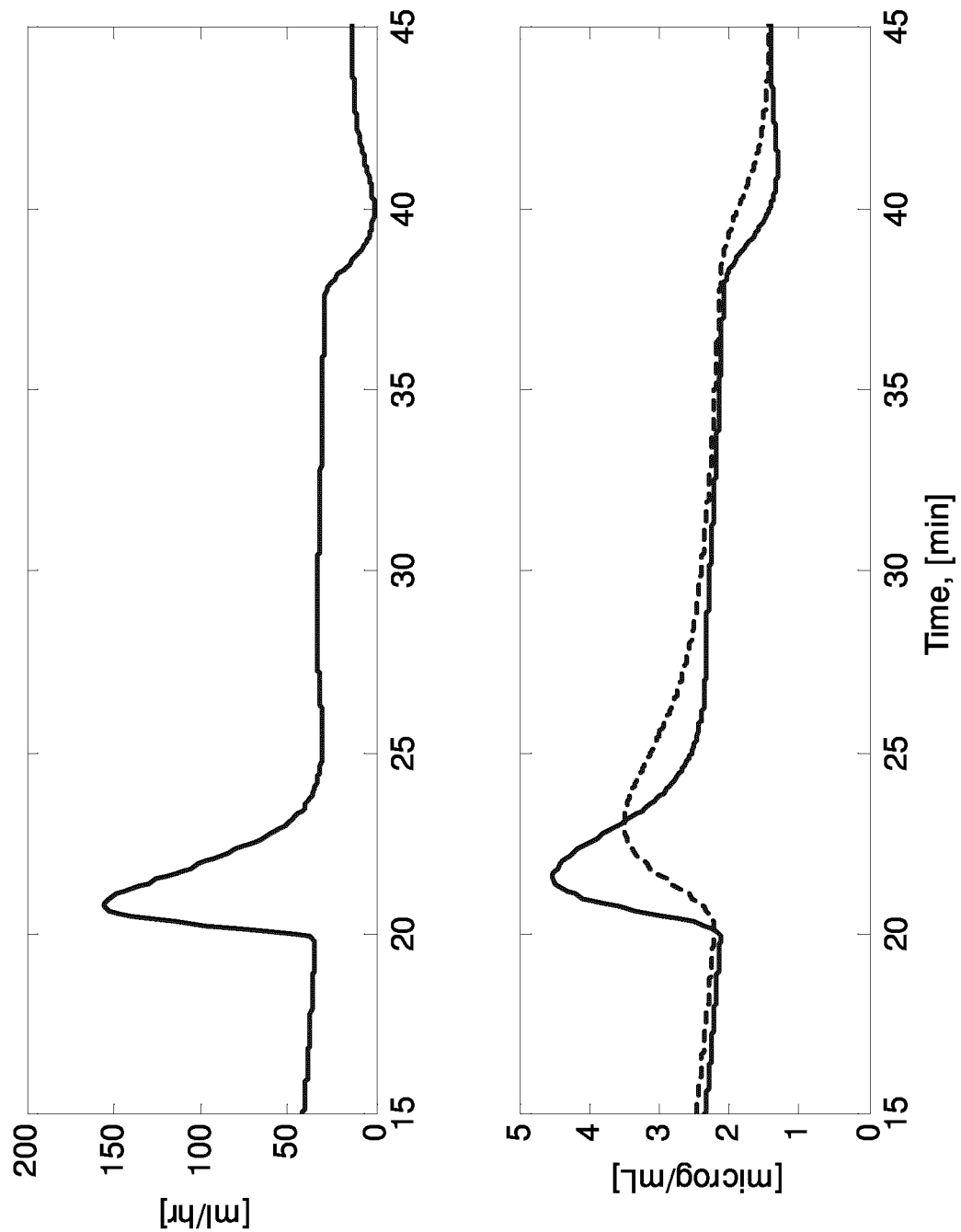
FIG. 7 illustrates the infusion rate and the predicted plasma concentration and effect-site concentration for a patient chosen for the study in the presence of disturbance from minutes 20 to 45.

At the start of a propofol infusion, after an increase in the infusion rate and/or after an administration of bolus, the concentration $C_p$ of drug in the plasma of patient 14A rises first. After a small delay, the concentration $C_e$ at the effect-site compartment increases until a maximum effect-site drug concentration is reached. When simulating this process, $C_p$ should be allowed to have a greater early stage (e.g. initial) concentration limit (constraint) than $C_e$. After $C_e$ has reached its steady-state concentration, the maximum constraint $Cp_{max}$ may be set equal to the maximum constraint $Ce_{max}$. Accordingly, after the initial spike in the plasma concentration $C_p$, the plasma concentration constraint may be modified (e.g. reduced) as the effect site concentration $C_e$ increases. This is shown in FIG. 7, which illustrates the administration of a propofol bolus, shown by an increase in infusion rate (top panel), the response of the plasma concentration $C_p$ (lower panel, solid line) and the effect site concentration $C_e$ (lower panel, dashed line). When the infusion is stopped or the infusion rate is reduced, the plasma propofol concentration $C_p$ falls first, the minimum concentration reached by $C_p$ may be lower than $C_e$. This effect is also shown in FIG. 7.

1) Effect-Site Concentration ($k_{e0}$ of EEG Monitor)

The effect site concentration $C_e$ parameter is representative of a drug concentration in the body of a patient which may correspond with a particular physiological characteristic. A PD model may provide a relationship between an effect site concentration $C_e$ of a particular drug and a level of characteristics in its corresponding physiological characteristic. In some embodiments, the effect site concentration $C_e$ estimated by auxiliary model 32 may correspond to the monitor 16A of system 30. In the case of the FIG. 6 embodiment, monitor 16A is a EEG monitor which provides a DOH monitor measurement. (In other particular embodiments, one or more monitors may be provided as monitor 16A in order to monitor multiple physiological characteristics). To predict $C_e$ in accordance with some such embodiments, equation (23) may be evaluated as explained in Schnider, T. W., C. F. Minto, et al. (1998), "*The influence of method of administration and covariates on the pharmacokinetics of propofol in adult volunteers*," Anesthesiology 88(5): 1170-1182 ("Schnider, Minto et al. 1998"), with $k_{e0}$ (18-60 yr:0.456 min⁻¹). A $C_e$ constraint is written as shown in equation (24A) as follows:

$$Ce_{min} \leq C_e \leq Ce_{max} \quad (24A)$$

$$Ce_{min} \leq \underbrace{[0 \ \underline{0 \ 0} \ 1]}_{C_{effect}} \cdot (Ax[k] + Bu[k]) \leq Ce_{max} \quad (24B)$$

where the effect site concentration $C_e$ may be estimated by auxiliary model 32 according to equation (24B) for the particular case of the 4-compartment PKPD model of equation (23).

To be compatible with the control algorithm (21), the constraints are rearranged in terms of $\Delta_u$:

$$C_e \leq Ce_{max} \Rightarrow C_{effect} \cdot B\Delta u[k] \leq Ce_{max} - (C_{effect} \cdot \underbrace{(Ax[k] + B(u[k-1]))}_{\Delta Ce}) \quad (25)$$

$$C_{min} \leq Ce \Rightarrow Ce_{min} - (C_{effect} \cdot \underbrace{(Ax[k] + B(u[k-1]))}_{\Delta Ce}) \leq C_{effect} \cdot B\Delta u[k]$$

2) Plasma Concentration

Following the same guidelines as those explained for $C_e$, in equations (24) and (25) the constraints for $C_p$ can be written as follows:

$$Cp_{min} \leq \underbrace{[1 \ \underline{0 \ 0} \ 0]}_{c_{plasma}} \cdot (Ax[k] + Bu[k]) \leq Cp_{max} \quad (26)$$

As explained above, the maximum and minimum limits for $C_p$ can change. From the values suggested in equations (19) and (20), some suitable constraints for $C_p$ may be as follows:

$$Cp_{max} = \text{Min} \left\{ \begin{array}{c} 10 \\ 7 + (7 - \Delta Ce) \end{array} \right. \quad (27)$$

$$Cp_{min} = \text{Max} \left\{ \begin{array}{c} 16 \\ 1.6 + (1.6 - \Delta Ce) \end{array} \right.$$

3) Blood Pressure ($K_{e0}$ of SBP)

As seen in FIG. 6, system 30 optionally includes one or more additional sensors 34 for monitoring an additional measurable physiological characteristic of the patient (e.g. in addition to the physiological characteristic that corresponds to the controlled variable and is sensed by monitor 16A (e.g. DOH, in the case of the illustrated FIG. 6 embodiment)). For example, in some embodiments, sensor 34 comprises a blood pressure sensor, and a physiological characteristic of patient 14A which may be measured during hypnosis is the systolic blood pressure (SBP) of the patient. The SBP values can themselves be used as constraints on the optimizations performed by controller 12A and/or they can be used to generate or refine the $C_p$, $C_e$ values determined by auxiliary model 32. An optional constraint to be considered in closed-loop control of hypnosis is the maximum drop in SBP during induction. This maximum drop in SBP may be particularly important for certain patients who are at higher risk of experiencing adverse side effects from anesthesia due to a change in SBP. Kazama et al. showed that the effect of propofol on the BIS DOH monitor (Aspect Medical Systems Inc. Norwood, MA, USA) occurs relatively rapidly compared with the effect of propofol on SBP (Kazama, Ikeda et al. 1999). To predict the effect site propofol concentration corresponding to the SBP, $C_{eBP}$, equation (23) may be calculated using the PK model (Schnider, Minto et al. 1998) in parallel with the patient model and $k_{e0}$ (20-39 yr: 0.1232 min$^{-1}$, 40-59 yr: 0.1182 min$^{-1}$ and 60-69 yr: 0.0778 min$^{-1}$) identified in Kazama, Ikeda et al. 1999. Kazama et al. expressed the effect of propofol on SBP as a percentage SBP decrease, SBP %, from baseline, SBP$_{base}$, to 80 mmHg as follows:

$$SBP_\% = \frac{SBP - 80}{SBP_{base} - 80} \cdot 100 = 100 - 100 \cdot \frac{Ce_{BP}[k]^\gamma}{EC50^\gamma + Ce_{BP}[k]^\gamma} \quad (28)$$

where EC50 is the propofol concentration associated with the 50% of maximum effect and y is the Hill coefficient.

For an optimization with respect to $\Delta u$ performed by controller 12A and subject to a lower bound (constraint) on SBP, it may be computationally efficient to establish a linear relationship between SBP and the effect-site propofol concentration $C_eBP$ corresponding to SBP. In some embodiments, the Hill equation (28) may be linearized around the point at which the SBP decreases from the baseline to the 50% point (i.e. a 50% decrease from baseline to 80 mmHg) with a constant slope of unity.

$$SBP_\% = 100 \cdot \frac{Ce_{BP}[k]}{2EC50} \quad (29)$$

Hypotension may be defined as a SBP drop of 50% from the baseline to 80 mmHg.

Optimization Steps Subject to the Constraints

The control objective of the FIG. 6 control system 30 is to minimize a performance index (cost function), J involving the difference between the desired DOH reference level r(k) and monitor measurement y(k) (e.g. the DOH WAV$_{CNS}$ measurement in the case of the illustrated embodiment) over a prediction horizon. This minimization may be performed at each time step k to determine the next control signal u(k). In particular embodiments, the minimization is performed subject to various constraints. As discussed elsewhere herein, the constraints may comprise one or more constraints on the concentrations estimated by auxiliary model 32. Auxiliary model 32 may model a physiological characteristic (e.g. SBP and/or the like) of patient 14A and auxiliary model 32 may map constraints on such physiological characteristics into corresponding constraints on the concentrations estimated by auxiliary model 32. The constraints on the optimization performed by controller 12A are not limited to constraints on concentrations estimated by auxiliary model 32. In some embodiments, controller 12A may additionally incorporate constraints based on other safety considerations for patient 14A and/or physical constraints on drug administrator actuator 13A and/or monitor 16A. In one particular non-limiting embodiment, optimization problem performed by controller 12A to minimize a cost function, J, has the form:

$$J = \sum_i^{n_p} \|y(k) - r(k)\|_Q^2 + \sum_0^{n_c-1} \|\Delta u(k)\|_R^2 \quad (30)$$

$$s.t. \begin{cases} 0 \leq u(k) \leq 600 \text{ mL/hr} \\ 1.6 \leq C_p(k) \leq 10 \text{ }\mu g/mL \\ 1.6 \leq C_e(k) \leq 7 \text{ }\mu g/mL \text{ or } SBP_\% \leq 50 \end{cases}$$

where $n_c$, the control horizon, is the number of samples used to capture the future control trajectory and $n_p$, the prediction horizon is the length of the optimization window, while Q and R are weights on the output error and incremental input respectively. In particular embodiments, the values for the estimated propofol plasma concentration ($C_p$) and estimated effect-site concentration ($C_e$) are estimated by auxiliary model 32. As discussed elsewhere herein, auxiliary model 32 may comprise a PKPD model (e.g. a population-based PKPD model, a patient-specific PKPD model based on the patient's personal history with the drug or some other type of PKPD model). In some embodiments, the concentrations (e.g. $C_e$ and $C_p$) estimated by auxiliary model 32 are related to physiological characteristics (e.g. like the DOH measured by monitor 16A, SBP measured by sensor 34 and/or the like). In this manner, auxiliary model 32 may be used to estimate values for evaluating physiological constraints which are projected back into the input space (e.g. concentration) of controller 12A when performing MPC optimization. In addition to or in the alternative to the foregoing, additional physiological characteristics (such as SBP and/or the like) may be measured from patient 14A and auxiliary model 32 may map these additional measured physiological characteristics and constraints based on these physiological characteristics into corresponding concentrations and constraints based on these corresponding concentrations. Additional constraints (not specifically related to auxiliary model 32) may be incorporated into the MPC optimizations performed by controller 12A. Such constraints may be related to safety considerations for patient 14A and/or physical limitations of hardware such as drug administration actuator 13A and/or monitor 16A, for example. For example, in the equation (30) optimization, a constraint limits the infusion rate, u between zero (as it is not possible to deliver a negative infusion rate) and a maximum infusion rate which is considered safe for the therapeutic window of the drug being administered (i.e. 600 mL/hr in the above example).

The function J and the constraints (30) can be rewritten in the following form:

$$J = \min_{\Delta U} \frac{1}{2}\Delta U^T H \Delta U + \Delta U^T f \quad (31)$$

$$M\Delta U \leq \Gamma$$

where M represents the constraints. The number of rows in the matrix M is equal to the number of constraints and the number of columns is equal to the dimension of $\Delta U$.

The inequality constraints may consist of active constraints and inactive constraints. The Kuhn-Tucker conditions define the active and inactive constraints in term of the Lagrange multipliers, $\lambda$. For an active constraint, the resultant $\lambda$ is positive and for a non-active constraint, $\lambda$ equals zero (Wang, L. (2009), "Model Predictive Control System Design and Implementation Using MATLAB®", London, Springer London). Some embodiments may make use of the dual active method, Hildreth's quadratic programming procedure (Hildreth, C. (1957), "A quadratic programming procedure," Naval Research Logistics Quarterly 4(1): 79-85) to systematically identify the constraints that are not active. The dual problem to the original quadratic problem may be expressed by:

$$J = \frac{1}{2}\lambda^T H \lambda + \lambda^T K + \frac{1}{2}\gamma^T E^{-1} \gamma \quad (32)$$

$$\text{s.t. } \lambda \geq 0$$

where $H=ME^{-1}M$ and $K=\gamma+ME^{-1}F$.

Let the optimal solution of this quadratic program be given by $\lambda^*$. Using Hildreth's algorithm, $\lambda^*$ can be obtained with successive optimization of each element of $\lambda$ separately:

$$\lambda_1^{m+1} = \max(0, \omega_i^{m+1}) \quad (33)$$

$$\omega_i^{m+1} = -\frac{1}{h_{ii}}\left[k_i + \sum_{j=1}^{i-1} h_{ij}\lambda_j^{m+1} + \sum_{j=i+1}^{n} h_{ij}\lambda_j^m\right],$$

where $h_{ij}$ is the ijth element in H and $k_i$ is the ith element in K.

An advantage of using Hildreth's algorithm is that it does not involve matrix inversion. In the event of conflict between constraints, the algorithm will deliver a compromise without terminating.

Tuning parameters of a typical MPC include $n_p$, $n_c$, R and Q. For the current system, the Kalman filter parameters, $R_w$ and $R_v$, may also be considered. For the unconstrained controller, the parameters were manually tuned for robustness with $n_p$=60, $n_c$=2, $R_w$=1, $R_v$=9, R=0.8.

Figure 13:
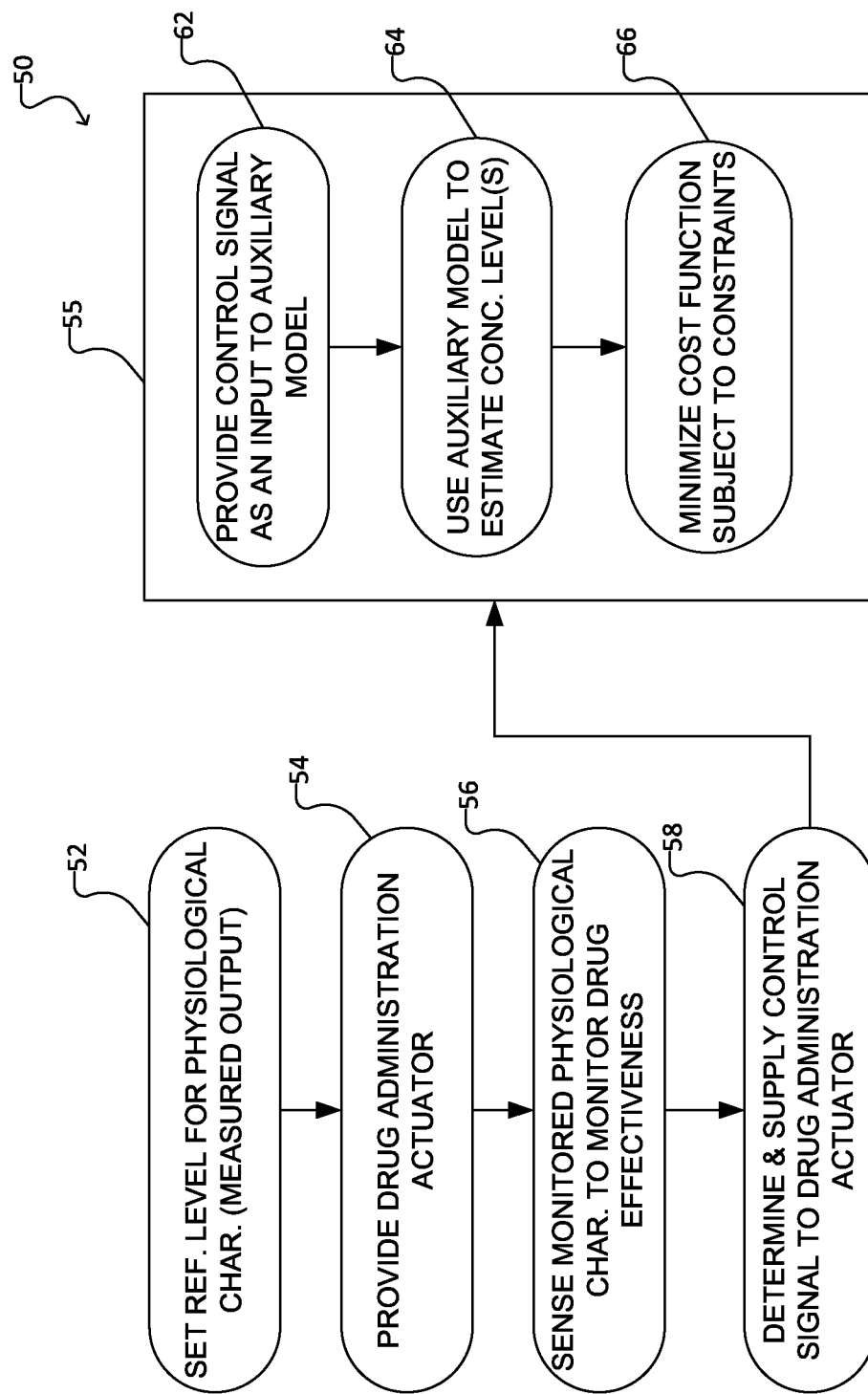
FIG. 13 is a flowchart of a method of closed-loop MPC control for the delivery of a drug, subject to constraints, according to one embodiment.

FIG. 13 is a flowchart of a method 50 for performing closed loop control of administration of at least one drug to a patient, to determine a control signal that can be provided to a drug administration actuator to controllably administer the drug to the patient. Method 50 can be performed with the use of an MPC control system, such as system 30 shown in FIG. 6. Method 50 comprises setting a reference level for one or more monitorable physiological characteristics (e.g. such as a depth of hypnosis obtained from a DOH monitor 16A), at block 52. In some embodiments, block 52 may comprise setting a reference trajectory which describes how a reference level changes over time. Method 50 further comprises providing a drug administration actuator (such as a controllable infusion pump or infusion syringe 13, a controllable drug inhalation device and/or the like), at block 54. Method 50 proceeds to block 56 by sensing the one or more monitored physiological characteristics of the patient and determining a monitor measurement indicative of an effect of the drug on the patient (e.g. in the case of administration of propofol or other hypnotic drug, block 56 may involve monitoring DOH of the patient). At block 58, method 50 comprises determining a control signal for the drug administration actuator and supplying the control signal to the drug administration actuator to cause the drug administration actuator to administer the drug to the patient at a drug dosage rate which causes the monitor measurement to track the block 52 reference level.

One example method 55 for determining a control signal at block 58 is shown in FIG. 13 (i.e. at blocks 62, 64 and 66). Method 55 comprises implementing a closed loop model-predictive control scheme which comprises, for each of the series of time steps, minimizing a cost function (performance index) subject to one or more constraints to thereby determine the control signal. The cost function is based at least in part on the reference level and the monitor measurement. In the illustrated embodiment, method 55 comprises using the control signal as an input to an auxiliary model (block 62); using the auxiliary model and the control signal to estimate at least one concentration level of the drug in the patient (block 64); and minimizing the cost function (performance index) subject to one or more constraints to determine the control signal (block 66). The constraints may comprise at least one constraint on the estimate of a concentration level of the drug as determined using the auxiliary model in block 64.

Figure 14:
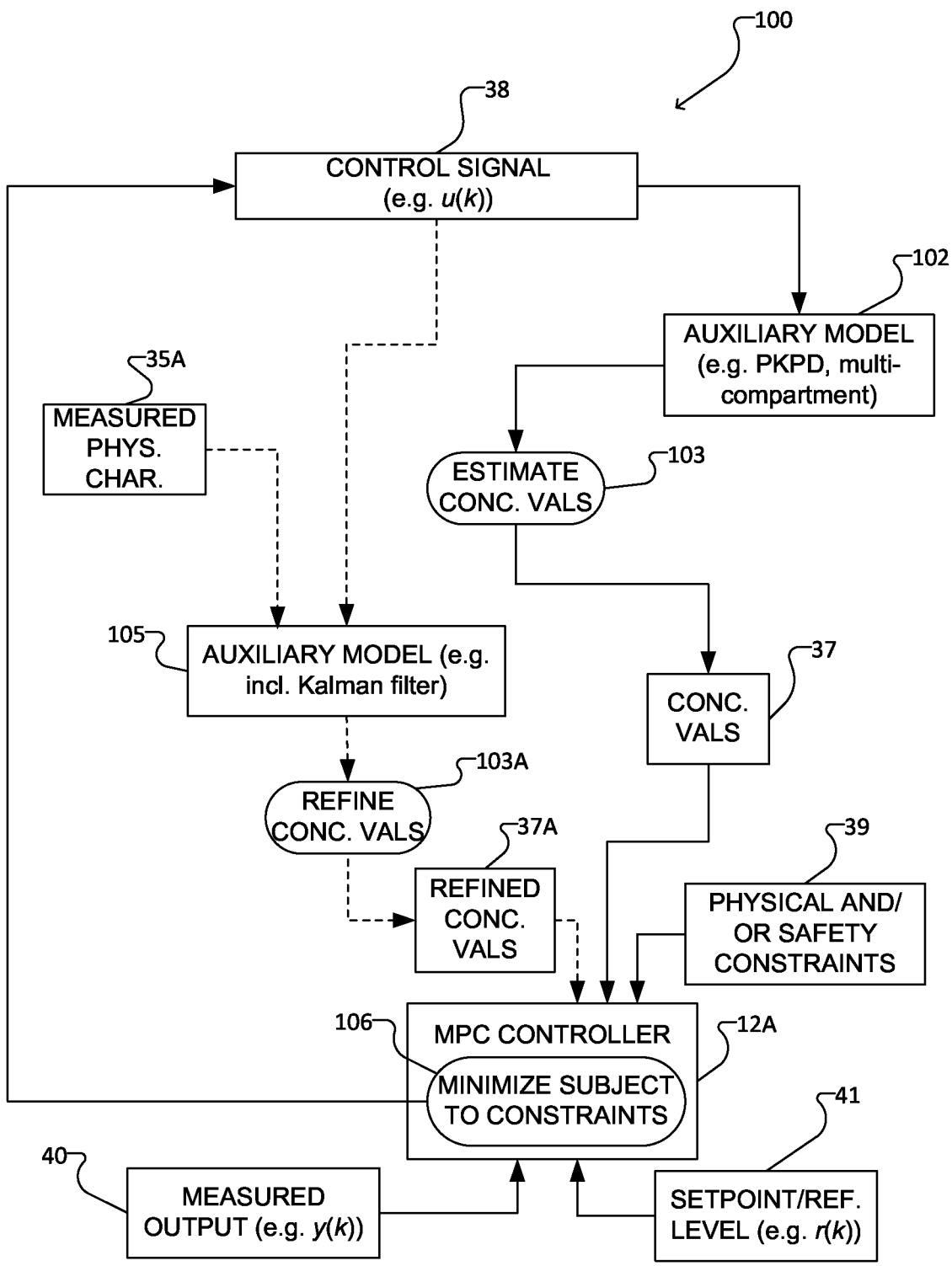
FIG. 14 is a flowchart showing a specific implementation of closed-loop MPC control for the delivery of a drug, subject to constraints, according to one embodiment.

FIG. 14 is a flowchart of a method 100 of performing closed-loop MPC control for delivery of a drug, subject to constraints on physiological characteristics and/or other parameters, according to one example embodiment. Method 100 can be performed by an MPC control system, such as system 30 shown in FIG. 6. Method 100 may be performed at least once in respect of each finite horizon T of the MPC controller. The output of method 100 is a control signal 38 (e.g. u(k)) provided to drug administrator actuator 13A to controllably administer a drug to the patient in accordance with the control signal 38. Method 100 begins by receiving a control signal 38 (e.g. an initialization value or the output of the previous iteration of method 100). For example, control signal 38 may be an infusion rate u(k) which is provided to a drug administration actuator 13A (e.g. syringe pump) of the FIG. 6 system 30. The control signal u(k) (including, optionally, its historical values) is input to an auxiliary model (e.g. auxiliary model 32 of the FIG. 6 system 30) at block 102, and using the auxiliary model together with the control signal u(k), the control system estimates, at block 103, values 37 for drug concentration levels in the patient. Drug concentration values 37 estimated by the auxiliary model may comprise estimates for the plasma concentration $C_p$ of a drug being administered, an effect site concentration $C_e$ corresponding to a monitored physiological characteristic 16A associated with the drug being administered (e.g. DOH) and/or an effect site concentration $C_e$ corresponding to some additional physiological characteristic of patient 14A that may be impacted by the drug being administered.. The auxiliary model 32 that is used to determine these values may comprise one or more of: a population-based model; a PKPD model; a population-based PKPD model; a multiple-compartment PKpd model; a multiple-compartment PKPD model, a patient-specific PKPD model, and/or the like. The auxiliary model 32 may comprise a model of any physiological characteristic that can be monitored, such as, for example, depth of hypnosis, blood pressure, cardiac output, heart rate variability, end tidal $CO_2$, respiratory rate, minute ventilation, end-tidal anesthetic agent monitoring and/or the like and may relate such physiological characteristics to corresponding drug concentrations (e.g. $C_p$, $C_e$). The auxiliary model 32 may make use of its one or more inputs (such as the control signal 38 (u(k) in the illustrated embodiment of FIG. 14) and its model corresponding to this physiological characteristic, which may then be used to determine drug concentration levels (or other characteristic that can be used to constrain the MPC controller 12A at block 106). In certain embodiments, the auxiliary model 32 may comprise a model of a depth of hypnosis (DOH) of the patient, and based on the input to the auxiliary model (i.e. control signal 38 (u(k)), the model may be used to determine values for plasma concentration $C_p$ and effect site concentration $C_e$ for the drug based on the DOH model. Further, user-configurable constraints expressed in terms of DOH may be converted by auxiliary model to 32 to constraints expressed in terms of these concentrations $C_p$ and/or $C_e$. In some embodiments, the auxiliary model 32 may comprise a model of systolic blood pressure (SBP) of the patient, and based on the input to the auxiliary model (i.e. control signal 38 (u(k)), the model may be used to determine values for plasma concentration $C_p$ and effect site concentration $C_e$ for the drug based on the SBP model. Further, user-configurable constraints expressed in terms of SBP may be converted by auxiliary model to 32 to constraints expressed in terms of these concentrations $C_p$ and/or $C_e$.

In addition (or in the alternative) to the steps at block 102, method 100 comprises providing one or more sensors (such as sensor 34 of the FIG. 6 system 30) for measuring an additional physiological characteristic of the patient and taking actual readings of measured sensor values 35A for the additional physiological characteristic at block 104A. These measured sensor values 35A can be input to an auxiliary model at block 105 and used at block 103A to refine the drug concentration values predicted by auxiliary model 32 to produce refined concentration values 37A. For example, auxiliary model 32 may comprise a Kalan filter or a state observer and/or the like. Additionally or alternatively, auxiliary model 32 may refine the drug concentration values previously obtained at block 103. In one particular example embodiment, the physiological characteristic that is measured by a sensor at block 104A is the systolic blood pressure (SBP) of the patient. The measured SBP values 35A can be input to an auxiliary model, comprising a Kalman filter for example, at block 105, to generate refined values 37A for $C_e$ and $C_p$.

Method 100 proceeds to block 106 which involves using estimated concentration values 37 for $C_e$ and $C_p$ (and/or refined values 37A for $C_e$ and $C_p$), which are now expressed in the input space for the MPC controller 12A, along with the output 40 of a monitor for measuring the response of the patient (e.g. DOH y(k)) and a reference level 41 set by the operator (e.g. DOH r(k)) to implement constrained MPC control. At block 106, the MPC controller 12A performs MPC minimization subject to constraints on the drug concentration levels in the patient and/or physiological characteristics and other parameters as described above with reference to equation (30). In the illustrated embodiment, the drug concentration values that are used to constrain the block 106 MPC minimization comprise the values 37 for $C_e$ and $C_p$ (or refined values 37A for $C_e$ and $C_p$). In addition, physical constraints and/or safety constraints 39 such as constraints on the infusion rate can be applied in the minimization step performed at block 106. The output 38 of method 100, determined as a result of performing the MPC optimization step at block 106, is a calculated control variable or infusion rate u(k) of the infusion pump.

Method 100 then repeats itself in considering the next finite horizon T and performing again the method steps starting at block 102 by using the auxiliary model to determine new predicted values 37 for $C_e$ and $C_p$. Method 100 may be repeated for subsequent time steps for the duration that closed-loop MPC control is required for controlling the delivery of propofol to the patient. One or more of the steps indicated through dotted flow lines (e.g. the steps performed at blocks 103A and 105) may be omitted in certain embodiments. For example, some embodiments of the method for closed-loop MPC control may not use measured SBP values, and may rely on the estimated concentration values 37 obtained through the auxiliary model at block 102 to provide constraints to the MPC cost minimization step at block 106.

The steps of method 100 may be implemented in software running on a suitable processor, in hardware incorporated in or accessible to a suitable processor, or in a mix of software and hardware. In particular embodiments, method 100 is implemented as software contained in a program memory accessible to a suitable processor. The processor implements the method by executing software instructions provided by the software. Such a processor may be integrated with other parts of a computer system or it may be implemented as a distinct component or system. Such processor, hardware and/or software may implement controller 12A and auxiliary model 32 of the FIG. 6 system 30.

The MPC-based systems and methods described herein including the FIG. 6 system 30 and the methods 50, 100 of FIGS. 13, 14 may be adapted for closed-loop MPC control of other substances that are administered into a body, such as other hypnotics, or analgesics, neuromuscular-blocking agents, hemodynamic medications, antihypertensive agents, analgesic adjuvants, neuroprotective drugs, anti-inflammatory agents, and/or the like. In such cases the concentration values and/or physiological characteristics that are obtained at blocks 103 and 104A and that are projected into the input space of the MPC controller to constrain the system at block 106 may be different, since for each type of drug, the evaluation of certain parameters may be more useful than others.

The methods and systems for constrained closed-loop MPC control may be expanded for use in controlling the simultaneous delivery of more than one drug to a patient. For example, in procedures conducted under anaesthesia, both a hypnotic (such as propofol as described in the above examples) and an analgesic (such as remifentanil) may be injected into the patient simultaneously, using separate syringe pumps for each substance. In such cases, the MPC control system 30 of FIG. 6 may be adapted to accept multiple inputs useful for the MPC optimization with these two substances (hypnotic and analgesic). These inputs may include the inputs and constraints already described above, with reference to method 100 of FIG. 14, that are used for control of the infusion of propofol (e.g. DOH y(k), reference DOH r(k) and physiological and physical constraints which may be estimated or otherwise evaluated using auxiliary model 32 which may project such constraints back into the input space of controller 12A), along with any additional inputs and constraints that are used for control of the infusion of an analgesic such as remifentanil. Such additional inputs and constraints for the administration of an analgesic may include, for example, the infusion rate u(k) for the drug (as an input for the MPC controller optimization, and as inputs to an auxiliary model to determine drug concentration levels such as plasma drug concentration values $C_p$) and constraints on the estimated drug concentration values. Performing the MPC minimization step with these inputs and subject to these constraints, the system 30 produces multiple outputs or control variables, namely, a rate of infusion for propofol and a rate of infusion for remifentanil.

Step 7: Monte Carlo Simulations and Results

Analytically proving the robustness of the FIG. 6 control system 30 in the presence of constraints provided by an auxiliary model may be complicated. For the purpose of evaluations conducted on the FIG. 6 control system 30, Monte Carlo simulations were used to observe the controller's robustness. Eight hundred and eighty random models were created by applying ±20% perturbations to all the PK and PD parameters of the patients in the study and generating 20 random models for each of the 44 individuals. The number of samples was determined by trial and error. In the evaluation, 10, 20, and 30 Monte-Carlo models (for each of the 44 individuals) were employed in simulating surgery scenarios. The results using 20 and 30 Monte-Carlo models were very close to each other and consistent upon repeating the simulation. To minimize the computation time while keeping the reliability of the results, the evaluation used 20 Monte-Carlo models per individual.

Figure 8:
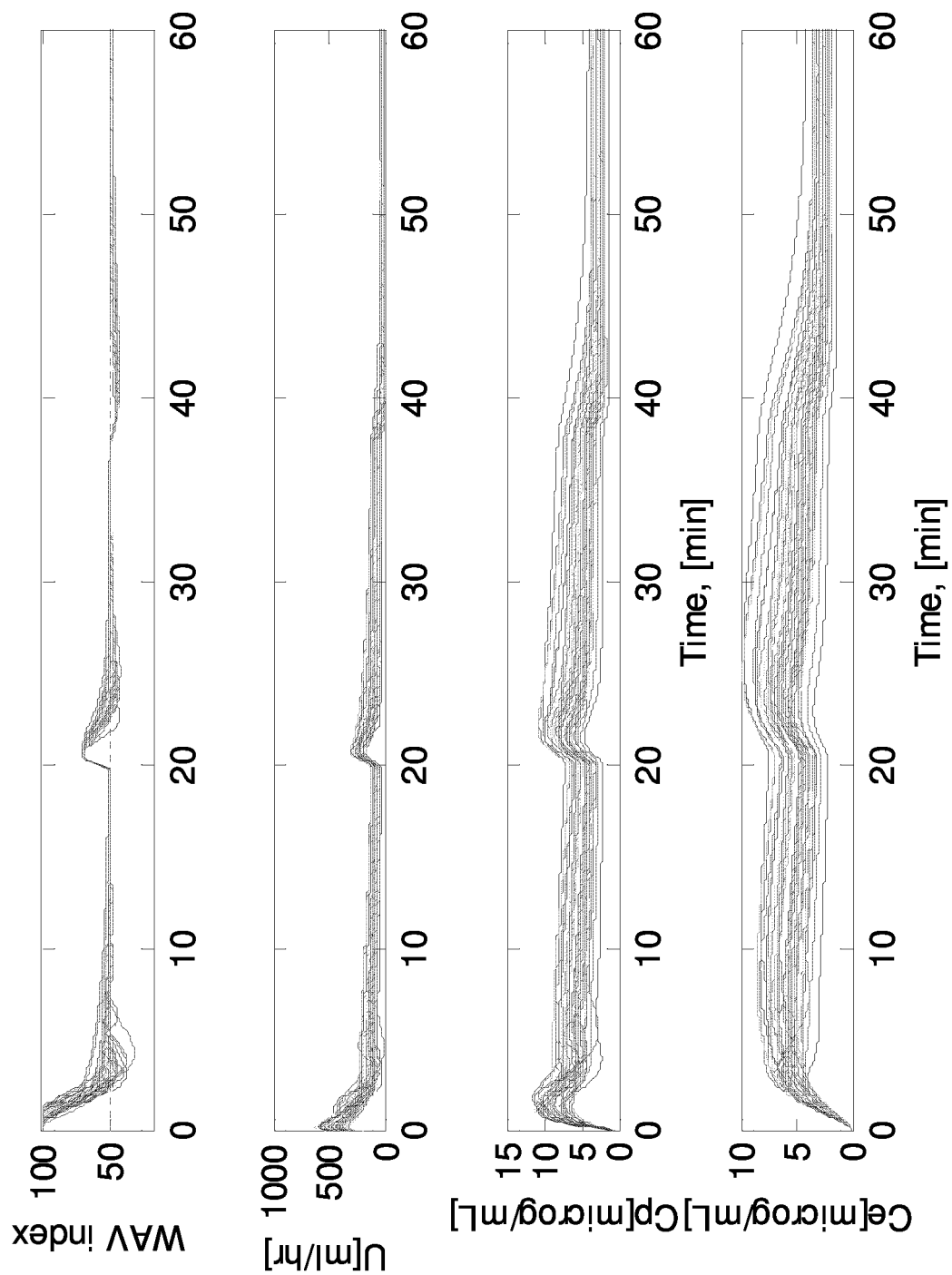
FIG. 8 illustrates a closed-loop MPC response of 44 patients with unconstrained MPC.
Figure 9:
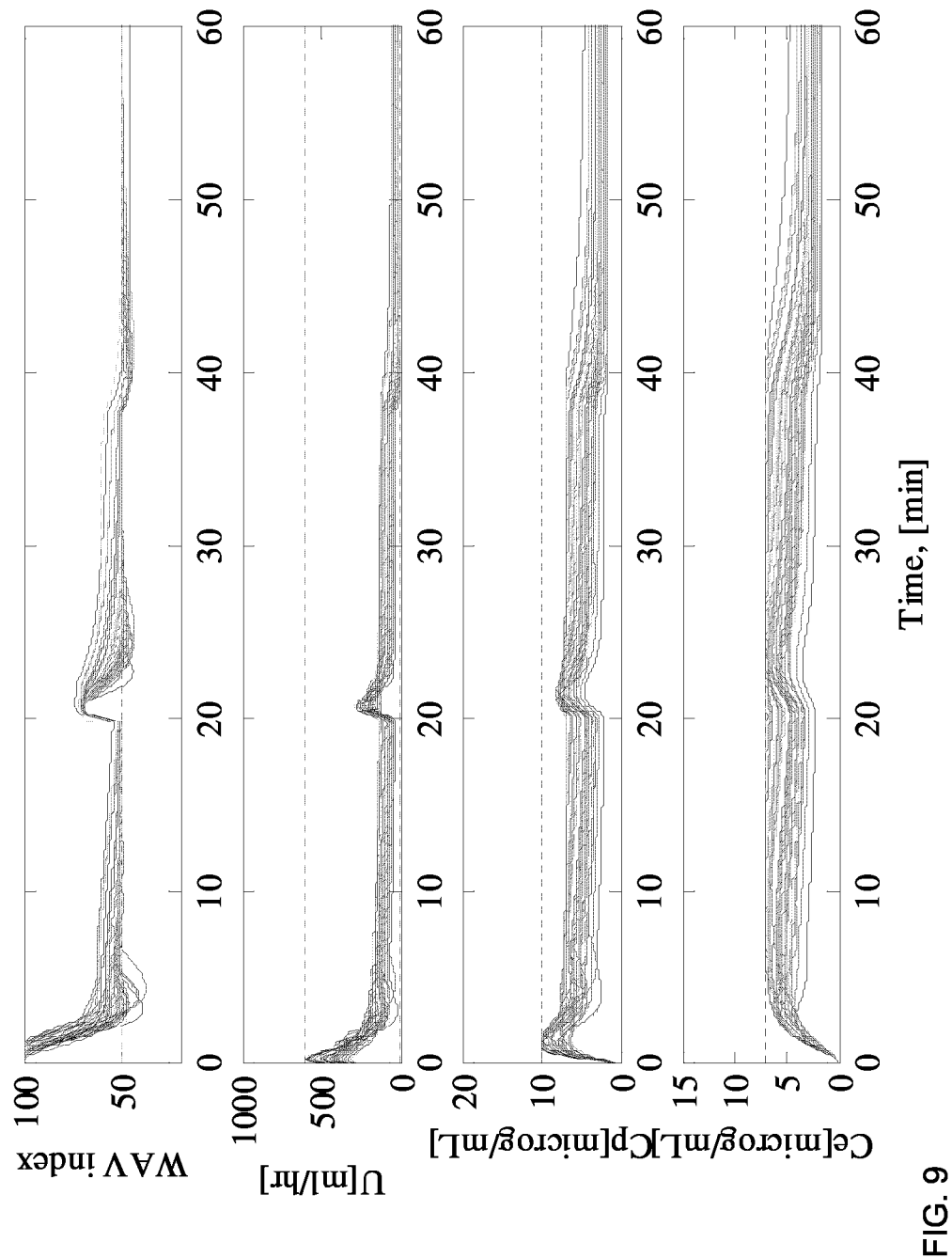
FIG. 9 illustrates a closed-loop MPC response of 44 patients using constrained MPC.

Induction time was defined as the time between the start of the propofol infusion and the time the $WAV_{CNS}$ first dropped below 60. Maintenance of anaesthesia was defined as the time between end of induction and the end of the propofol infusion. In controller tuning, a design specification is to minimize the time to induction and system overshoot during induction while improving response to stimulation without compromising patient safety. Simulated induction of anaesthesia was completed in an average (SD) of 3.4(2.0) minutes with reference level overshoot ($WAV_{cns}$<50) of 2.7% (6.1) for the constrained MPC. Comparing those results with the ones obtained with the unconstrained MPC, (induction time 2.9(0.9) minutes and overshoot of 3.7% (7.5) demonstrates that safety constraints can be added to the control system for hypnosis without significantly increasing the rise time. Results obtained with an unconstrained MPC emphasize the benefits of incorporating the concentration constraints in the MPC controller, as they show that without these constraints, 39% of patients would reach $C_p$>10 µg/ml and 36% of patients would reach $C_e$>7 µg/ml, (see FIGS. 8 and 9 which respectively show a closed-loop MPC response of 44 patients with unconstrained MPC and constrained MPC). These high concentrations may result in significant drops in SBP and may also increase the incidence of burst suppression (BS).

Figure 10:
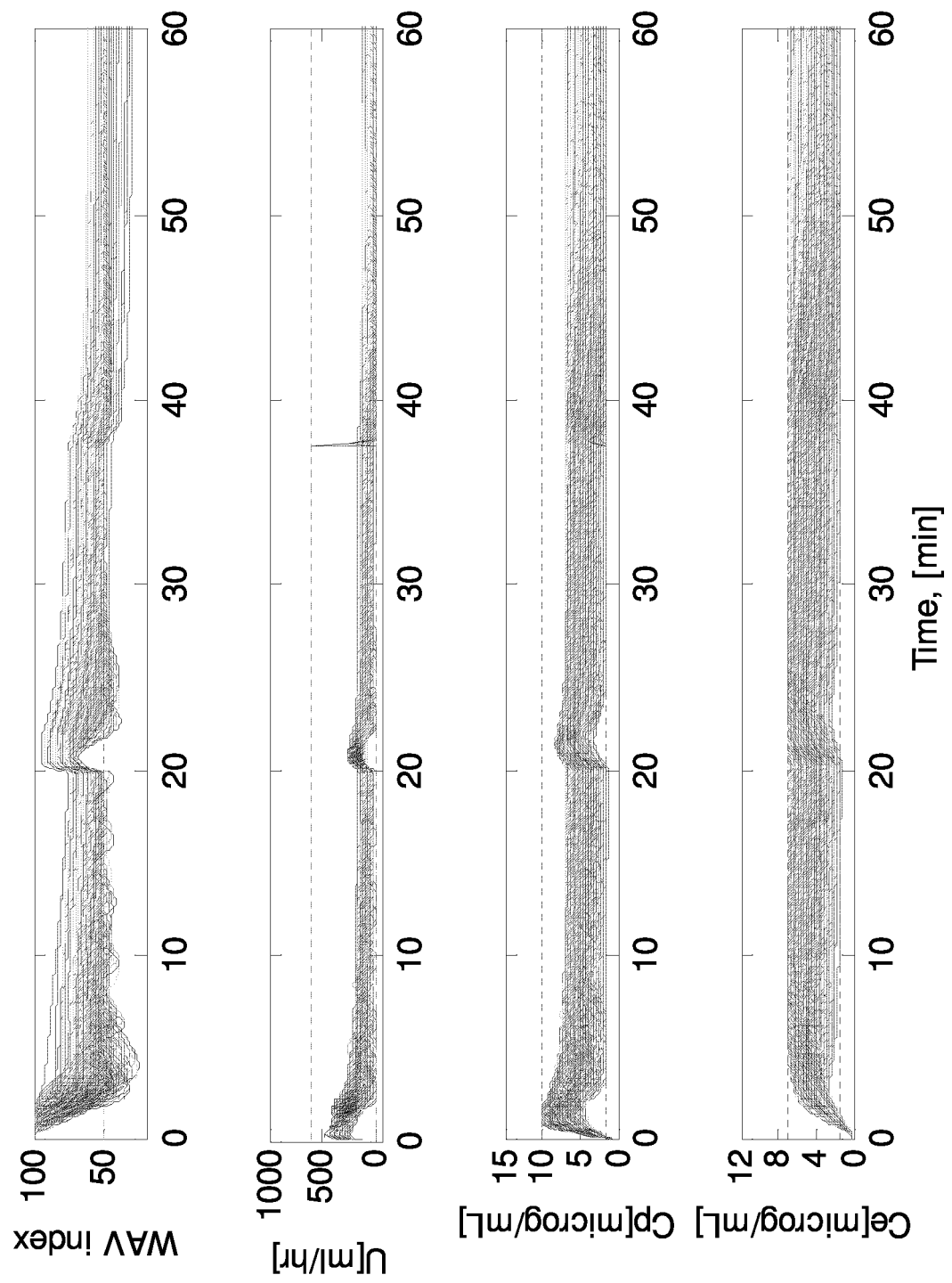
FIG. 10 illustrates a closed-loop constrained MPC response of 880 Monte Carlo simulated patients.

FIG. 10 shows the results of Monte Carlo simulations for 880 random patient models conducted on the constrained closed-loop MPS control system 30 of FIG. 6. The control system is shown to be robust with the ±20% uncertainties to the PK and PD parameters and in the presence of simulated disturbance. The ±20% uncertainties resulted in numerous patients which are far from the average population and are considered outliers. These were patients with very long delays, very slow or very fast clearance, etc. When coming across such cases, often identified during induction, anesthesiologists may modify referenced levels and/or constraint values, which in return should improve the performance.

Figure 11:
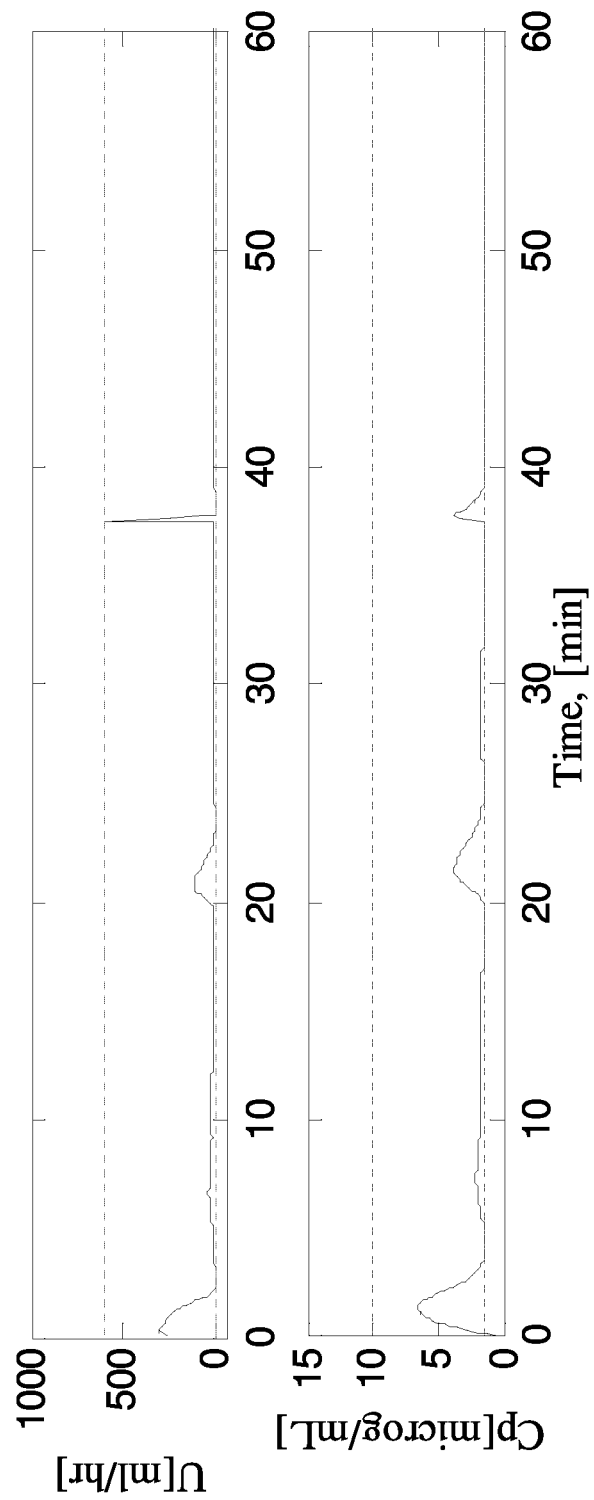
FIG. 11 illustrates a closed-loop MPC response for a patient in the study where a conflict between constraints resulted in a compromised solution.

Using Monte Carlo simulations, a few cases were encountered where due to conflict between constraints, Hildreth's quadratic programming technique was forced to deliver a compromised solution. A compromise on the infusion rate constraint may result in a value outside the physical limit of the pump. However, this may be avoided by incorporating a physical constraint on the infusion rate. FIG. 11 shows an example of this situation, in a closed-loop MPC response for a patient in the study where a conflict between constraints, u<600 ml/hr and Cp>1.6, resulted in a compromised solution. The resulting u around 37 minutes was restrained with a physical constraint, namely, the maximum infusion rate allowable by the pump.

Figure 12A:
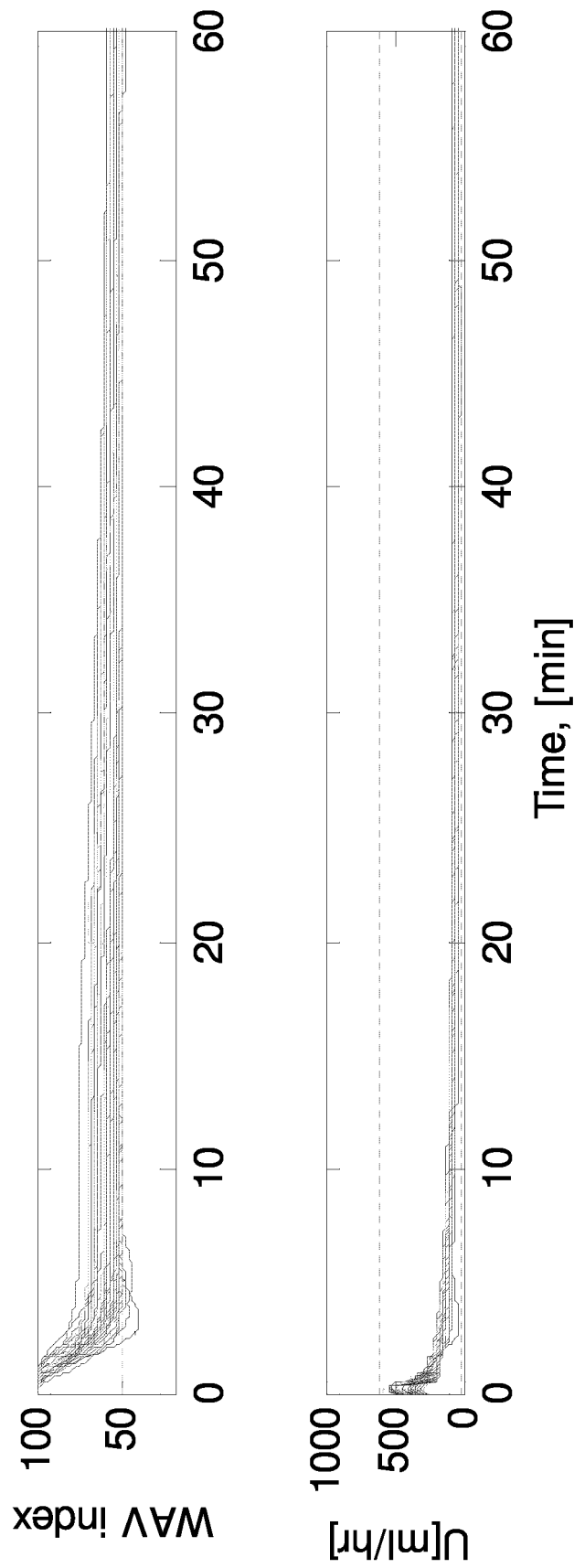
FIG. 12A illustrates closed-loop MPC response of 44 patients with systolic blood pressure (SBP) limit of 50%. The percent SBP drop in from baseline to 80 mmHg are shown for a constrained system (FIG. 12B) and an unconstrained system (FIG. 12C).
Figure 12C:
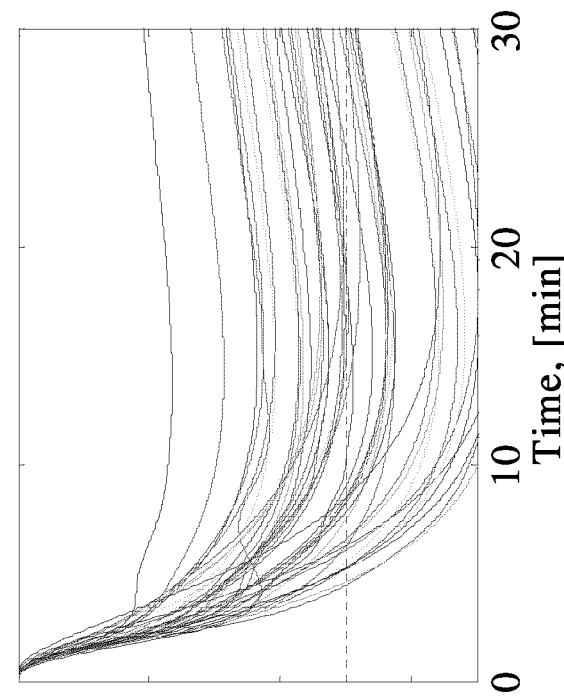
Figure 12B:
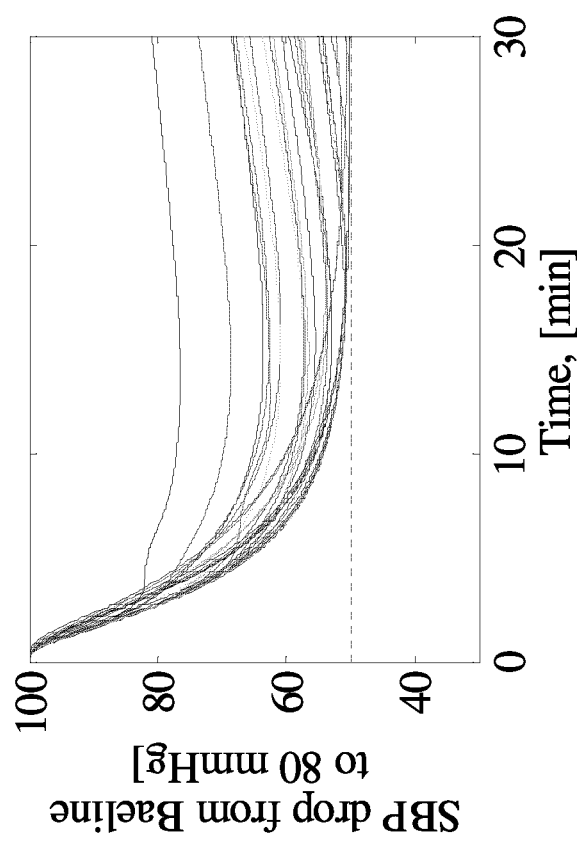

FIG. 12A shows the results of SBP constraint on the closed-loop MPC response of 44 patients with systolic blood pressure (SBP) limit of 50% with no disturbance. FIGS. 12B and 12C show the percent SBP drop from baseline to 80 mmHg with BSP constrained MPC and unconstrained MPC respectively. These results demonstrate that the implemented constraint was effective in controlling the SBP above the limit. These results were achieved at the expense of a slower induction as shown in Table 4.

TABLE 4

| MPC Controller | Rise-Time [min] | Overshoot [%] |
| --- | --- | --- |
| Unconstrained | 2.9 ± 0.9 | 3.7 ± 7.5 |
| Constrained | 3.4 ± 2.0 | 2.7 ± 6.1 |

Rise-Times is defined as time in minutes required for $WAV_{cns}$ to fall below 60 and Overshoot as the $WAV_{cns}$ index below the set-point of 50.

Delivery of opioids to the patient may reduce the amount of propofol required, causing greater clinical effects than would be expected with propofol alone (Vuyk, J., M. J. Mertens, et al. (1997), "*Propofol anesthesia and rational opioid selection: determination of optimal EC50-EC95 propofol-opioid concentrations that assure adequate anesthesia and a rapid return of consciousness*," Anesthesiology 87(6): 1549-1562). As appreciated by persons of skill in the art, in the presence of surgical stimuli, patients may tolerate higher propofol concentrations without experiencing serious cardiovascular side effects. Due to these influences, the values selected as safety bounds (constraints) in accordance with particular embodiments can be adjusted as needed to factor in age, ASA (American Society of Anesthesiologists) status, known medical history, opioids use, intensity of expected stimuli, and other considerations. As demonstrated by the evaluations conducted in respect of the present technology, there are benefits to imposing constraints in the application of closed-loop control of the administration of drugs to a patient and in particular in the implementation of a closed-loop MPC to control the delivery of anesthesia drugs. The present technology introduces the implementation of physiological constraints in closed-loop control of hypnosis using MPC with a parallel PKPD model. Evaluation of this MPC controller during simulated induction and maintenance of anesthesia shows that the design specifications were satisfied. The constrained control strategy can potentially reduce the risk of under- or overdosing for most patients by providing controller enforced safety bounds.

Interpretation of Terms

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms.
Embodiments of the invention (including the control systems and/or methods described herein) may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a computer system for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Embodiments of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

The invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a controller, software module, processor, server, client, device, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

While a number of exemplary aspects and embodiments have been discussed above, those of skill in the art will recognize certain modifications, permutations, additions and sub-combinations thereof.

As such, the scope of the claims should not be limited by the preferred embodiments set forth in the examples, but should be given the broadest interpretation consistent with the description as a whole.

What is claimed is:

1. A control system for closed loop control of administration of at least one drug to a patient, the control system comprising:
a drug administration actuator connectable to a source of the at least one drug and to a patient for administration of the at least one drug to the patient at a controllable drug dosage rate;
one or more monitors for sensing one or more monitored physiological characteristics of the patient and determining therefrom a monitor measurement indicative of an effect of the at least one drug on the patient; and
a processor configured, for each of a series of time steps, to determine a control signal and supply the control signal to the drug administration actuator to thereby cause the drug administration actuator to administer the at least one drug to the patient at a drug dosage rate which causes the monitor measurement to track a reference level;
wherein the processor is configured to implement a closed loop model-predictive control scheme which comprises, for each of the series of time steps, minimizing a cost function (performance index) subject to one or more constraints to thereby determine the control signal, the cost function based at least in part on the reference level and the monitor measurement;
wherein the processor is configured to use the control signal as an input to an auxiliary model and to use the auxiliary model and the control signal to estimate at least one concentration level of the at least one drug in the patient; and
wherein the one or more constraints comprise at least one constraint on the estimate of the at least one concentration level of the at least one drug.

2. The control system of claim 1 wherein the processor is configured to implement a robust model-predictive control scheme wherein the robust model-predictive control scheme causes the monitor measurement to track the reference level despite inter-patient variability within a population with respect to the effect of the at least one drug.

3. The control system of claim 2 wherein processor is configured to implement the robust model-predictive control scheme by using a nominal model that has been tuned with respect to quantified inter-patient uncertainty.

4. The control system of claim 3 wherein the nominal model is based on a combination of models from the population, with each model representing an effect of the drug on a corresponding member of the population.

5. The control system of claim 4 wherein the combination of models comprises an average of the models over the population.

6. The control system of claim 1 wherein the drug administration actuator comprises a controllable drug injection device.

7. The control system of claim 6 wherein the processor is configured, for each of the series of time steps, to determine the control signal and supply the control signal to the controllable injection device to thereby cause the controllable injection device to administer the at least one drug to the patient at a drug infusion rate which causes the monitor measurement to track the reference level.

8. A control system for closed loop control of administration of at least one drug to a patient, the control system comprising:
a drug administration actuator connectable to a source of the at least one drug and to a patient for administration of the at least one drug to the patient at a controllable drug dosage rate;
one or more monitors for sensing one or more monitored physiological characteristics of the patient and determining therefrom a monitor measurement indicative of an effect of the at least one drug on the patient; and
a processor configured, for each of a series of time steps, to determine a control signal and supply the control signal to the drug administration actuator to thereby cause the drug administration actuator to administer the at least one drug to the patient at a drug dosage rate which causes the monitor measurement to track a reference level;
wherein the processor is configured to implement a closed loop model-predictive control scheme which comprises, for each of the series of time steps, minimizing a cost function (performance index) subject to one or more constraints to thereby determine the control signal, the cost function based at least in part on the reference level and the monitor measurement;
wherein the processor is configured to use the control signal as an input to an auxiliary model and to use the auxiliary model and the control signal to estimate at least one concentration level of the at least one drug in the patient; and
wherein the drug dosage rate which the processor causes the drug administration actuator to administer is effected by varying a volume and/or concentration of the drug in a liquid or gas.

9. The control system of claim 8 wherein the processor is configured to implement a robust model-predictive control scheme wherein the robust model-predictive control scheme causes the monitor measurement to track the reference level despite inter-patient variability within a population with respect to the effect of the at least one drug.

10. The control system of claim 9 wherein processor is configured to implement the robust model-predictive control scheme by using a nominal model that has been tuned with respect to quantified inter-patient uncertainty.

11. The control system of claim 10 wherein the nominal model is based on a combination of models from the population, with each model representing an effect of the drug on a corresponding member of the population.

12. The control system of claim 11 wherein the combination of models comprises an average of the models over the population.

13. The control system of claim 8 wherein the drug administration actuator comprises a controllable drug injection device.

14. The control system of claim 13 wherein the processor is configured, for each of the series of time steps, to determine the control signal and supply the control signal to the controllable injection device to thereby cause the controllable injection device to administer the at least one drug to the patient at a drug infusion rate which causes the monitor measurement to track the reference level.

15. A method for implementing closed loop controlled administration of at least one drug to a patient, the method comprising:

provaging a drug administration actuator for administration of the at least one drug to the patient at a controllable drug dosage rate;

sensing one or more physiological characteristics of the patient and determining therefrom a monitor measurement indicative of an effect of the at least one drug on the patient; and for each of a series of time steps, determining a control signal and supplying the control signal to the drug administration actuator to thereby cause the drug administration actuator to administer the at least one drug to the patient at a drug dosage rate which causes the monitor measurement to track a reference level;

wherein determining the control signal comprises implementing a closed loop model-predictive control scheme which comprises, for each of the series of time steps, minimizing a cost function (performance index) subject to one or more constraints to thereby determine the control signal, the cost function based at least in part on the reference level and the monitor measurement;

wherein determining the control signal comprises using the control signal as an input to an auxiliary model and using the auxiliary model and the control signal to estimate at least one concentration level of the at least one drug in the patient; and wherein the one or more constraints comprise at least one constraint on the estimate of the at least one concentration level of the at least one drug.

16. The method of claim 15 wherein implementing the closed loop model-predictive control scheme comprises implementing a robust model-predictive control scheme wherein the robust model-predictive control scheme causes the monitor measurement to track the reference level despite inter-patient variability within a population with respect to the effect of the at least one drug.

17. The method of claim 16 wherein implementing the robust model-predictive control scheme comprises using a nominal model that has been tuned with respect to quantified inter-patient uncertainty.

18. The method of claim 17 wherein the nominal model is based on a combination of models from the population, with each model representing an effect of the drug on a corresponding member of the population.

19. The method of claim 18 wherein the combination of models comprises an average of the models over the population.

20. The method of claim 15 wherein the drug administration actuator comprises a controllable drug injection device.

* * * * *